United States Patent
Ford et al.

(10) Patent No.: US 6,878,516 B1
(45) Date of Patent: Apr. 12, 2005

(54) AUTOREGULATORY SYSTEM FOR VALIDATING MICROBIAL GENES AS POSSIBLE ANTIMICROBIAL TARGETS USING A TETRACYCLINE-CONTROLLABLE ELEMENT

(75) Inventors: Charles W. Ford, Portage, MI (US); Cheryl L. Quinn, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/600,392

(22) PCT Filed: Jan. 12, 1999

(86) PCT No.: PCT/US99/00371
§ 371 (c)(1),
(2), (4) Date: Sep. 8, 2000

(87) PCT Pub. No.: WO99/36554
PCT Pub. Date: Jul. 22, 1999

Related U.S. Application Data
(60) Provisional application No. 60/071,640, filed on Jan. 16, 1998.

(51) Int. Cl.[7] .............................. C12Q 1/68; C12Q 1/02; A61K 49/00; C12N 15/00; C07H 21/04
(52) U.S. Cl. ..................... 435/6; 435/69.1; 435/69.7; 435/29; 435/320.1; 435/235.1; 435/325; 435/252.3; 536/23.1; 536/24.1; 424/9.1
(58) Field of Search .................... 435/6, 69.1, 69.7, 435/29, 320.1, 235.1, 325, 252.3; 536/23.1, 24.1; 424/9.1

(56) References Cited

U.S. PATENT DOCUMENTS

| 5,362,646 A | 11/1994 | Bujard et al. |
| 5,464,758 A | 11/1995 | Gossen et al. |
| 5,589,362 A | 12/1996 | Bujard et al. |
| 5,650,298 A | 7/1997 | Bujard et al. |
| 5,654,168 A | 8/1997 | Bujard et al. |
| 5,891,670 A * | 4/1999 | Burnham et al. .......... 435/69.1 |
| 6,309,669 B1 * | 10/2001 | Setterstrom et al. ........ 424/486 |

FOREIGN PATENT DOCUMENTS

| DE | 44 17 598 A1 | 12/1995 |
| WO | WO 94/29442 | 12/1994 |
| WO | WO 96/01313 | 1/1996 |
| WO | WO 96/40946 | 12/1996 |
| WO | WO 96/40979 | * 12/1996 |
| WO | WO 99/36554 | 7/1999 |

OTHER PUBLICATIONS

Nesin et al. 1990, Antimicrobial Agents and Chemotherapy, vol. 34, pp. 2273–2276.*

Brown et al., "Signature–tagged and directed mutagenesis identify PABA synthetase as essential for *Aspergillus fumigatus* pathogenicity," *Mol Microbiol.* Jun. 2000;36(6):1371–1380.

Hensel et al., "Simultaneous identification of bacterial virulence genes by negative selection," *Science*. Jul. 21, 1995;269(5222):400–403.

(Continued)

*Primary Examiner*—Gerry Leffers
(74) *Attorney, Agent, or Firm*—Peter C. Richardson; Gregg C. Benson; Irene M. Reininger

(57) ABSTRACT

A screen has been designed to genetically engineer microbial pathogens so that expression of specific genes can be regulated in vitro and during host infection to facilitate the identification of bacterial genes essential for maintaining an infection. Specifically, gene regulatory elements which respond to the presence or absence of tetracycline are used to regulate the expression of endogenous bacterial genes. Because tetracycline is not normally present in animals, a tetracycline-regulated microbial gene can be controlled in vivo by adding or removing tetracycline from the infected animals' diet.

22 Claims, 14 Drawing Sheets

OTHER PUBLICATIONS

Shea et al., "Identification of a virulence locus encoding a second type III secretion system in *Salmonella typhimurium,*" *Proc Natl Acad Sci USA*. Mar. 19, 1996;93(6):2593–2597.

N. H. Albretson et al., "Construction and use of a new vector/transposon, pLBT:: mini–TN10:lac:kan, to identify environmentally responsive genes in a marine bacterium," *FEMS–Microbiology Letters, 140*:287–294 (1996).

M.G. Bayer, et al., "The Molecular Architecture of the sar Locus in *Staphylococcus aureus,*" *Journal of Bacteriology, 178*:4563–4570 (1996).

A. Camilli et al., "Use of genetic recombination as a reporter of gene expression," *Proceedings of the National Academy of Sciences USA, 91*:2634–2638 (1994).

A. M. Campbell, "Episomes," *Advances in Genetics, vol. 11*, Caspari et al., eds., Academic Press, New York, pp. 101–145 (1962).

A. K. East et al., "Cloning and Sequence Determination of Six *Staphylococcus aureus* β–Lactamases and Their Expression in *Escherichia coli* and *Staphylococcus aureus,*" *Journal of General Microbiology, 135,* 1001–1015 (1989).

K. Gan et al., "Isolation and Characterization of a Temperature–sensitive Mutant of *Salmonella typhimurium* Defective in Prolipoprotein Modification," *The Journal of Biological Chemistry, 268*:16544–16550 (1993).

K. Gan et al., "The umpA Gene of *Escherichia coli* Encodes Phosphatidylglycerol:Prolipoprotein Diacylglyceryl Transferase (lgt) and Regulates Thymidylate Synthase Levels through Translational Coupling," *Journal of Bacteriology, 177*:1879–1882 (1995).

M. Geissendörfer et al., "Regulated expression of heterologous genes in *Bacillus subtilis* using the Tn10 encoded tet regulatory elements," *Applied Microbiology and Biotechnology, 33*:657–663 (1990).

P. Ghersa et al., "Highly controlled gene expression using combinations of a tissue–specific promoter, recombinant adenovirus and a tetracycline–regulatable transcription factor," *Gene Therapy, 5*:1213–1220 (1998).

M. Gossen et al., "Tight control of gene expression in mammilian cells by tetracycline–responsive promoters," *Proceedings of the National Academy of Sciences USA, 89*:5547–5551 (1992).

M. Gossen et al., "Transcriptional Activation by Tetracyclines in Mammalian Cells," *Science, 268*:1766–1769 (1995).

M. Hensel et al., "Simultaneous Identification of Bacterial Virulence Genes by Negative Selection," *Science, 269,* 400–403 (1995).

W. Hillen et al., "Nucleotide sequence of the Tn10 encoded tetracycline resistance gene," *Nucleic Acids Research, 11*:525–539 (1983).

W. Hillen et al., "7: Tet repressor–tet operator interaction," *Protein–Nucleic Acid Interaction, vol. 10,* Saeger et al., eds., MacMillan, London, pp. 143–162 (1989).

S. Iordanescu, "Characterization of the *Staphylococcus aureus* chromosomal gene pcrA, identified by mutations affecting plasmid pT181 replication," *Molecular and General Genetics, 241*:185–192 (1993).

S. Iordanescu et al., "Two Restriction and Modification Systems in *Staphylococcus aureus* NCTC8325," *Journal of General Microbiology, 96*:277–281 (1976).

H. J. Kim et al., "Tetracycline Repressor–Regulated Gene Repression in Recombinant Human Cytomegalovirus," *Journal of Virology, 69*:2565–2573 (1995).

L. Kim et al., "A xylose–inducible *Bacillus subtilis* integration vector and its application," *Gene, 181*:71–76 (1996).

D. J.C. Knowles, "New strategies for antibacterial drug design," *Trends in Microbiology, 5*:379–383 (1997).

F. W. F. Lee et al., "Application of Ty1 for cloned gene insertion: amplification of a large regulated expression cassette in *Saccharomyces cerevisiae,*" *Applied Microbiology and Biotechnology, 44*:620–623 (1996).

M. J. Mahan et al., "Antibiotic–based selection for bacterial genes that are specifically induced during infection of a host," *Proceedings of the National Academy of Sciences USA, 92:* 669–673 (1995).

J. M. Mei et al., "Identification of *Staphylococcus aureus* virulence genes in a murine model of bacteraemia using signature–tagged mutagenesis," *Molecular Microbiology, 26*:399–407 (1997).

G. Miksch et al., "The kil gene of the ColE1 plasmid of *Escherichia coli* controlled by a growth–phase–dependent promoter mediates the secretion of a heterologous periplasmic protein during the stationary phase," *Archives of Microbiology, 167*:143–150 (1997).

National Center for Biotechnology Information, National Library of Medicine, National Institutes of Health, Genbank AA248779 Accession No. J1830.seq.F, "Human fetal heart, Lambda ZAP Express *Homo sapiens,*" [online]. Bethesda, MD [retrieved on Jan. 18, 2001]. Retrieved from the Internet:<URL:http://www.ncbi.nlm.nih.gov/query.fcgi?cmd=Retrieve&db=Nucleotide&list_uids=1880210&dopt=GenBank>, 2 pages.

National Center for Biotechnology Information, National Library of Medicine, National Institutes of Health, Genbank Locus PI25BLAZA Accession No. M15526, "Plasmid pI258 (from *S. aureus*) beta–lactamase (blaZ), complete cds," [online]. Bethesda, MD [retrieved on Jan. 18, 2001]. Retrieved from the Internet:<URL:http://www.ncbi.nlm.nih.gov/query.fcgi?cmd=Retrieve&db=Nucleotide&list_uids=150716&dopt=GenBank>, 2 pages.

National Center for Biotechnology Information, National Library of Medicine, National Institutes of Health, Genbank Locus STATETM Accession No. M21136, "*S. aureus* tetracycline resistance (tetM) gene, complete cds," [online]. Bethesda, MD (1990) [retrieved on Jan. 18, 2001]. Retrieved from the Internet:<URL:http://www.ncbi.nlm.nih.gov/query.fcgi?cmd=Retrieve&db=Nucleotide&list_uids=153114&dopt=GenBank>, 2 pages.

National Center for Biotechnology Information, National Library of Medicine, National Institutes of Health, Genbank Locus SAFEMA Accession No. X17688–M23918, "*S. aureus* factor essential for expression of methicillin resistance (femA) gene, complete cds, and trpA gene, 3'end.," [online]. Bethesda, MD [retrieved on Jan. 18, 2001]. Retrieved from the Internet:<URL:http://www.ncbi.nlm.nih.gov/query.fcgi?cmd=Retrieve&db=Nucleotide&list_uids=46579&dopt=GenBank<, 3 pages.

National Center for Biotechnology Information, National Library of Medicine, National Institutes of Health, Genbank Locus SAU35773 Accession No. U35773, "*Staphylococcus aureus* prolipoprotein diacylglyceryl transferase (lgt) gene, complete cds," [online]. Bethesda, MD [retrieved on Feb. 28, 2001]. Retrieved from the Internet:<URL:http://www.ncbi.nlm.nih.gov/query.fcgi?cmd=Retrieve&db=Nucleotide&list_uids=1016769&dopt=GenBank>, 2 pages.

M. Nesin et al., "Cloning and Nucleotide Sequence of a Chromosomally Encoded Tetracycline Resistance Determinant, tetA(M), from a Pathogenic, Methicillin–Resistant Strain of *Staphylococcus aureus*," *Antimicrobial Agents and Chemotherapy,* 34:2273–2276 (1990).

T. Ngueyn et al., "Sequence homology between the tetracycline–resistance determinants of Tn10 and pBR322," *Gene,* 25:83–92 (1983).

R. P. Novick et al., "pT181 Plasmid Replication Is Regulated by a Countertranscript–Driven Transcriptional Attenuator," *Cell,* 59:395–404 (1989).

K. Okada et al., "The ispB Gene Encoding Octaprenyl Diphosphate Synthase is Essential for Growth of *Escherichia Coli*," *Journal of Bacteriology,* 179:3058–3060 (1997).

H. L. Peng et al., "Cloning, Characterization, and Sequencing of an Accessory Gene Regulator (agr) in *Staphylococcus aureus*," *Journal of Bacteriology,* 170:4365–4372 (1988).

K. Postle et al., "Nucleotide sequence of the repressor gene of the TN10 tetracycline resistance determinant," *Nucleic Acids Research* 12:4849–4863 (1984).

W. C. Raschke et al., "Inducible expression of a heterologous protein in *Hansenula polymorpha* using the alcohol oxidase 1 promoter of *Pichia pastoris*," *Gene,* 177:163–167 (1996).

G. Ramakrishnan et al., "A tetracycline–inducible gene expression system in *Entamoeba histolytica*," *Molecular and Biochemical Parasitology,* 84:93–100 (1997).

F. Rivero et al., "*Dictyostelium discoideum* Cells Lacking the 34,000–Dalton Actin–binding Protein Can Grow, Locomote, and Develop, but Exhibit Defects in Regulation of Cell Structure and Movement: A Case of Partial Redundancy," *The Journal of Cell Biology,* 135:965–980 (1996).

E. Selva et al., "Targeted Screening for Elongation Factor Tu Binding Antibiotics," *The Journal of Antibiotics,* 50:22–26 (1997).

A. Skerra, "Use of the tetracycline promoter for the tightly regulated production of a murine antibody fragment in *Escherichia coli*," *Gene,* 151:131–135 (1994).

A. M. Strandén et al., "Cell Wall Monoglycine Cross–Bridges and Methicillin Hypersusceptibility in a femAB Null Mutant of Methicillin–Resistant *Staphlococcus aureus*," *Journal of Bacteriology,* 179:9–16 (1997).

M. Takahashi, "Kinetic and Equilibrium Characterization of the Tet Repressor–Tetracycline complex by Fluorescence Measurements," *Journal of Molecular Biology,* 187:341–348 (1986).

K. Tovar et al., "Identification and nucleotide sequence of the class E tet regulatory elements and operator and inducer binding of the encoded purified Tet repressor," *Molecular and General Genetics,* 215:76–80 (1988).

B. Unger et al., "Nucleotide sequence of the repressor gene of the RA1 tetracycline resistance determinant: structural and functional comparison with three related Tet repressor genes," *Nucleic Acids Research,* 12:7693–7703 (1984).

B. Unger et al., "Nucleotide sequence of the gene, protein purification and characterization of the pSC101–encoded tetracycline resistance–gene–repressor," *Gene,* 31:103–108 (1984).

P. Z. Wang et al., "Nucleotide Sequence and Expression of the β–Lactamase Gene from *Staphylococcus aureus* Plasmid pI258 in *Escherichia coli, Bacillus subtilis,* and *Staphylococcus aureus*," *Journal of Bacteriology,* 169:1763–1766 (1987).

S. H. Waters et al., "The tetracycline resistance determinants of RP1 and Tn1721:nucleotide sequence analysis," *Nucleic Acids Research,* 11:6089–6105 (1983).

F. Yao et al.; "Tetracycline Repressor, tetR, rather than the tetR–Mammalian Cell Transcription Factor Fusion Derivatives, Regulates Inducible Gene Expression in Mammalian Cells," *Human Gene Therapy,* 9:1939–1950 (1998).

* cited by examiner

Fig. 2

```
                    sarA terminator
KpnI   ------------>         <------------ terminator
ggtaccgaagtttgatagatgatacattctattaaacttccttttttat
|---------|---------|---------|---------|-------- 50
ccatggcttcaaactatctactatgtaagataatttgaaggaaaaaata gctctgaaaaaacaatgattatctaccttattagtgcagatagataacca
|---------|---------|---------|---------|--------- 100
cgagactttttgttactaatagatggaataatcacgtctatctattggt
  terminator----------------->         <-----------
                                pcrB terminator XmaI
ttgtttatcccggg
|---------|--- 114
aacaaatagggccc
------
```

SEQ. I.D. 33

Fig. 3

```
XmaI
cccgggtaggacacaatatccacttgtagtttataataacgatctcctcc    50
tttccactttaattcaaatctatattaaagaatatttcatcttatttaat   100
aagaaaccatatttatataacaacataaaacgcactaagttattttattg   150
aacatatatcttactttatctatccgactatttagacgacgggtctggca   200
aacaggttcgccagtggtaacctgatatccttttagctctgctaaacaaa   250
cactaagcccatttgtaaaaaagttaaatcattgcgataatcttgaata    300
catcgagcaggaatttctccaataataatgacctcattattttcagttg    350
agtatttacgatatttgcacaatatttgggagcatcgttatatgcccgtg   400
aaagatattcctgtggtgcataaactttaaaactaagatatggctctaac   450
aattctgttccagcttttctaaaggcttgctccagtacaataggagtaag   500
catccgaaaatctgctggagtactaacagggctatagtataaaccgtact   550
taaaacagattttacaatccgtcacattccaaccatataatccttgttcg   600
caaccatagcgtatcccttccataactgcattttgaaatgattgatttaa   650
gtatccaagagaaaccgagctctcatactgcattccacttcccaacggaa   700
gcggtgatacagataaaccaatggaagcccagaaaggatttggcggcact   750
tcgatgtgaatggtatattctgcatttttaacggtctctccatataaat    800
gactgtaggctcttttagttctatctccacatgatacttttcttgcaaca   850
gtgcactaatcacttccatttgtactttccctaagaaagaaagtataatt   900
tcatgtgtcgtagaatccacgtaatatcgtagaagcggatcactatctga   950
gatttccaaaagggcatcaagcaacatttctctctgttcaggtttactcg  1000
gttcaacagttgtttgtagtagagggtgcggattttcaatcttttttctc  1050
tgtggcaatagttttgtatctccaagaacactatttaacttcaaaaactc  1100
attttgcaaaataacaatttctccagaataagctctatcaatcttacata  1150
attcaccatttattgaagtatacatttctgtaacttttattttttctttt  1200
tctgatactctaaccgaatctcgtaaatgtagtactccactataaaggcg  1250
tatatatgcaagacgttgtctttttttgtatattcaattttgaaaacat   1300
ttccgcaaagttcagacggacctcgatgtgttgatgaataaaatttatta  1350
gtaataacttctataaggttatcaatccctatattacttttgcacttcc   1400
atgataaagagggaacagagaacaattctgaaatcttatgctttcctctt  1450
gttcgagttccaatgcttctaatgatttaccggacatatatttctctaaa  1500
aggtcatcgtttccctctattaccgtatcccattgttcagattcggtaaa  1550
gttcgtcacacacatattaggatacagttctaccttctgtttgattacaa  1600
tttcggcagaaagtttctctttaatatcctgataaaccgttgataaatca  1650
attccattttggtcaatcttattgataaaaagattgtgggaatcccat    1700
tttcctaagtgcatgaaataatatacgagtttgtgcttgtacgaaatctt  1750
ttgcagaaatcagtagaattgccccatctaaaactgataatgaacgatat  1800
acttctgctaagaaatccatatgtcctggcgtgtctatgatgttcacctt  1850
cgtattttcccactgaaaagaggttattcctgtctgaattgtaattcctc  1900
tctgacgttctaaaagcgtattatccgtcctcgttgtacctttgtccacg  1950
cttcctaattctgtaatcgctccactgttatataataagctttctgttaa  2000
ggtagtttttcctgcatcaacatgagctaaaactccaatattaataattt  2050
tcatgtgatttcctccattggatcc                           2076
                        BamHI
```

SEQ. I.D. 34

Fig. 4A

BamHI
```
ggatccttaagacccactttcacatttaagttgtttttctaatccgcata    50
tgatcaattcaaggccgaataagaaggctggctctgcaccttggtgatca   100
aataattcgatagcttgtcgtaataatggcggcatactatcagtagtagg   150
tgtttccctttcttctttagcgacttgatgctcttgatcttccaatacgc   200
aacctaaagtaaaatgccccacagcgctgagtgcatataatgcattctct   250
agaaaaaccttgttggcataaaaaggctaattgattttcgagagtttcat   300
actgtttttctgtaggccgtgtacttttgctccatcgcgatgacttagta   350
aagcacatctaaaacttttagcgttattacgtaaaaaatcttgccagctt   400
tccccttctaaagggcaaaagtgagtatggtgcctatctaacatctcaat   450
ggctaaggcgtcgagcaaagcccgcttattttttacatgccaatacaatg   500
taggctgctctacacctagcttctgggcgagtttacgggttgttaaacct   550
tcgattccgacctcattaagcagctctaatgcgctgttaatcactttact   600
tttatctaatctaga                                      615
        XbaI
```

SEQ. I.D. 35

Fig. 4B

*BamHI*
```
ggatccttaagacccactttcacatttaagttgttttttctaatccgcata    50
tgatcaattcaaggccgaataagaaggctggctctgcaccttggtgatca    100
aataattcgatagcttgtcgtaataatggcggcatactatcagtagtagg    150
tgtttccctttcttctttagcgacttgatgctcttgatcttccaatacgc    200
aacctaaagtaaaatgccccacagcgctgagtgcatataatgcattctct    250
agaaaaaccttgttggcataaaaaggctaattgattttcgagagtttcat    300
actgtttttctgtaggccgtgtacttttgctccatcgcgatgacttagta    350
aagcacatctaaaacttttagcgttattacgtaaaaaatcttgccagctt    400
tccccttctaaagggcaaaagtgagtatggtgcctatctaacatctcaat    450
ggctaaggcgtcgagcaaagcccgcttattttttacatgccaatacaatg    500
taggctgctctacacctagcttctgggcgagtttacggggttgttaaacct    550
tcgattccgacctcattaagcagctctaatgcgctgttaatcactttact    600
```

*XbaI*
```
tttatctaatctagacatcattaattcctaattttgttgacgacactct     650
atcattgatagagttatttgtcaaactagt                         680
                              SpeI
```

SEQ. I.D. 36

Fig. 5

```
        XbaI                                              tetO
        tctagacatcattaattcctccttttttgttgacACTCTATCATTGATAGA
        |---------|---------|---------|---------|---------   50
        agatctGTAgtaattaaggaggaaaaacaactgTGAGATAGTAACTATCT
            <-Met                           -10
                                               P_tet SpeI
        GTtatttgtcaaactagttttttatttgtcgagttcatgaaaaactaaaa
        |---------|---------|---------|---------|---------  100
        CAataaacagtttgatcaaaaaataaacagctcaagtacttttttgatttt
               -35

P_xyl
            -35                   -10                   PstI
        aaaattgacACTCTATCATTGATAGAGTataattaaaataaaaaagctgc
        |---------|---------|---------|---------|---------  150
        ttttaactgTGAGATAGTAACTATCTCAtattaatttttatttttttcgacg
                            tetO
        ag
        |-  152
        tc
```

SEQ. I.D. 37

Fig. 6A

```
PstI
ctgcagcggagggtttatttt gaaaaagttaatatttttaattgtaattg     50
ctttagttttaagtgcatgtaattcaaacagttcacatgccaaagagtta    100
aatgatttagaaaaaaatataatgctcatattggtgtttatgctttaga    150
tactaaaagtggtaaggaagtaaaatttaattcagataagagatttgcct    200
atgcttcaacttcaaaagcgataaatagtgctatttt gttagaacaagta    250
ccttataataagttaaataaaaagtacatattaacaaagatgatatagt    300
tgcttattctcctattttagaaaaatatgaggaaaagatatcactttaaa    350
agcacttattgaggcttcaatgacatatagtgataatacagcaaacaata    400
aaattataaagaaatcggtggaatcaaaaaagttaaacaacgtctaaaa    450
gaactaggagataaagtaacaaatccagttagatatgagatagaattaaa    500
ttactattcaccaaagagcaaaaagatacttcaacacctgctgctttcg    550
gtaagactttaaataaacttatcgcaatggaaaattaagcaaagaaaac    600
aaaaaattcttacttgatttaatgttaaataataaaagcggagatacttt    650
aattaaagacggtgttccaaaagactataaggttgctgataaaagtggtc    700
aagcaataacatatgcttctagaaatgatgttgcttttgtttatcctaag    750
ggccaatctgaacctattgttttagtcatttttacgaataaagacaataa    800
aagtgataagccaaatgataagttgataagtgaaaccgccaagagtgtaa    850
tgaaggaatttta agaattcgcatgc                           876
      EcoRI SphI
```

SEQ. I.D. 38

Fig. 6B

```
PstI
ctgcagcggagggtttatttttgaaaaagttaatatttttaattgtaattg      50
ctttagttttaagtgcatgtaattcaaacagttcacatgccaaagagtta      100
aatgatttagaaaaaaatataatgctcatattggtgtttatgctttaga       150
tactaaaagtggtaaggaagtaaaatttaattcagataagagatttgcct      200
atgcttcaacttcaaaagcgataaatagtgctatttgttagaacaagta       250
ccttataataagttaaataaaaagtacatattaacaaagatgatatagt       300
tgcttattctcctattttagaaaatatgaggaaaagatatcactttaaa       350
agcacttattgaggcttcaatgacatatagtgataatacagcaaacaata      400
aaattataaaagaaatcggtggaatcaaaaaagttaaacaacgtctaaaa      450
gaactaggagataaagtaacaaatccagttagatatgagatagaattaaa      500
ttactattcaccaaagagcaaaaagatacttcaacacctgctgctttcg       550
gtaagactttaaataaacttatcgcaatggaaaattaagcaaagaaaac       600
aaaaaattcttacttgatttaatgttaaataataaaagcggagatacttt      650
aattaaagacggtgttccaaaagactataaggttgctgataaaagtggtc      700
aagcaataacatatgcttctagaaatgatgttgcttttgtttatcctaag      750
ggccaatctgaacctattgttttagtcatttttacgaataaagacaataa      800
aagtgataagccaaatgataagttgataagtgaaaccgccaagagtgtaa      850
tgaaggaattttaagtttaaac                                  872
                   PmeI
```

SEQ. I.D. 39

Fig. 7A

*SacI*
```
cagctctttcagaaatttcggttatgcaacatcattacgttcaaacactc   50
aaggtcgcggtacttacactatgtacttcgatcactatgctgaagttcca  100
aaatcaatcgctgaagatattatcaagaaaaataaaggtgaataatataa  150
cttgttttgactagctagcctaggttaaaatacaaggtgagcttaaatgt  200
aagctatcatctttatagtttgattttttggggtgaatgcattataaaag  250
aattgtaaaattcttttttgcatcgctataaataatttctcatgatggtga  300
gaaactatcatgagagataaatttggtacc                      330
                              KpnI
```

SEQ. I.D. 40

Fig. 7B

```
PmeI
gtttaaacgaataggagagatttttataatggcaaaagaaaaattcgatcg      50
ttctaaagaacatgccaattcggtacttcggtcacgttgaccatggtaaa      100
acaacattaacagcaatcgctactgtattagcaaaaaatggtgactcagt      150
tgcacaatcatatgacatgattgacaacgctccagaagaaaaagaacgtg      200
gtatcacaatcaatacttctcacattgagtaccaaactgacaaacgtcac      250
tacgctcacgttgactgcccaggacacgctgactacgttaaaaacatgat      300
cactggtgctgctcaaatggacggcggtatcttagtagtatctgctgctg      350
acggtccaatgccacaaactcgtgaattcgcatgc                    385
                                EcoRI SphI
```

SEQ. I.D. 41

Fig. 8A

*Sac*I
gagctcggttgcagatggcattgtcattggtagcgaaatcgttaagcgat   50
ttaaatctaacacgcgtgaggaaatcattaaatatttacaatctatccaa   100
caaacattgaataattaagtttacttgatttaaaaaaattaggcgaatac   150
tgtttgaaaaagtgaaaaacggtgaattataaaattgaatacaatttcaa   200
aaaaagtaatatgagcaaacccaaacgttcatattactttttttgaaatt   250
gtattcaaaaatctaaatattactataaaagtatacgcaattaaagcgtt   300
tatgttttagttttaacattaactattgtacttatttagattagattt   350
attattttgacatttgcagaggggtacc   379
                      *Kpn*I

SEQ. I.D. 42

Fig. 8B

```
         PmeI
gtttaaactgcaaatacggaaatgaaattaattaacgagagacaaatagg     50
agtaatgataatgaagtttacaaatttaacagctaaagagtttggtgcct    100
ttacagatagcatgccatacagtcatttcacgcaaactgttggccactat    150
gagttaaagcttgctgaaggttatgaaacacatttagtgggaataaaaaa    200
caataataacgaggtcattgcagcttgcttacttactgctgtacctgtta    250
tgaaagtgttcaagtattttattcaaatcgcggtccagtgattgattat     300
gaaatcaagaactcgtacacttttctttaatgaattatcaaaatatgt      350
taaaaaacatcgttgtctatacctacatatcgatccatatttaccatatc    400
aatacttgaattcgcatgcg                                  420
         EcoRI SphI
```

SEQ. I.D. 43

Fig. 9A

*SacI*
```
gagctcgggttcaatattaactgaaaagaattagattaaatattaattt    50
ggaaaactggaacaaccaaaaagttatatgaccgcgtaggtcttaatgaa  100
gagacgctaagtattttagatactgaaatcactaaaaaaacaatacctgt  150
aagacctggtagaaatgttgcggtaattattgaggtcgctgcaatgaact  200
atcgattaaatatcatgggcattaacactgccgaagaatttagtgaaaga  250
ttaaatgaagaaattatcaagaacagtcataagaggtacc            290
                                        KpnI
```

SEQ. I.D. 44

Fig. 9B

```
PmeI
gtttaaacggaggagtaggttgaatgggtattgtatttaactatatagat      50
cctgtggcatttaacttaggaccactgagtgtacgatggtatggaattat     100
cattgctgtcggaatattacttggttactttgttgcacaacgtgcactag     150
ttaaagcaggattacataaagatactttagtagatattatttttatagt      200
gcactatttggatttatcgcggcacgaatctatttgtgattttccaatg      250
gccatattacgcggaaaatccaagtgaaattattaaaatatggcatggtg     300
gaatagcaatacatggtggtttaataggtggctttattgctggtgttatt    350
gtatgtaaaggaaaaatttaaacccatttcaaattggtgatatcgttgcg     400
ccaagtataattttagcgcaaggaattcgcatgc                      434
                         EcoRI SphI
```

SEQ. I.D. 45

SEQUENCE LISTING

<160> NUMBER OF SEQ ID NOS: 45

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 1
acgcacgagc tcggttgcag atggcattgt c                                       31

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 2
ggggtacccc ctctgcaaat gtcaaa                                             26

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 3
acgcacgagc tcagatcttc gcttgtgcgg                                         30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 4
ggggtacccg ctgaagagat agcgattg                                           28

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 5
acgcacgagc tctttcagaa atgttcggtt atg                                     33

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 6

```
ggggtaccaa atttatctct catgatag                                          28

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 7
caggtacagc agtaagtaag c                                                 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 8
gtcaacgtga gcgtagtgac g                                                 21

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 9
cgaagtttga tagatgatac attctattaa acttcctttt tttatgctct gaaa             54

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 10
aaacaatgat tatctacctt attagtgcag atagataacc attgtttatc                  50

<210> SEQ ID NO 11
<211> LENGTH: 52
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 11
agcataaaaa aaggaagttt aatagaatgt atcatctatc aaacttcggt ac               52

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 12
```
ccgggataaa caatggttat ctatctgcac taataaggta gataatcatt gtttttttcag     60

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 13
cgggatccaa tggaggaaaa tcacatg     27

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 14
tcccccgggg taggacacaa tatccacttg tag     33

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 15
gactagtttg acaaataact ctatcaatga tagagtgtc     39

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 16
taatgatgtc tagattagat aaaagt     26

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 17
cgggatcctt aagacccact ttcacattt     29

<210> SEQ ID NO 18
<211> LENGTH: 62
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 18
ctagacatca ttaattcctc cttttttgttg acactctatc attgatagag ttatttgtca     60

```
aa                                                              62

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 19
ctagtttgac aaataactct atcaatgata gtgtcaacaa aaaggaggaa ttaatgatgt    60

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 20
ctagtttttt atttgtcgag ttcatgaaaa actaaaaaaa attgac                    46

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 21 tttttttag ttttcatga actcgacaaa taaaaaa                                37

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 22
actctatcat tgatagagta taattaaaat aaaaaagctg ca                        42

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 23
acatacgcat gcgaattctt aaaattcctt cattacactc                           40

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 24
```

```
gctttttttat tttaattata ctctatcaat gatagagtgt caa          43
```

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 25

```
aactgcagta atatcggagg gtttattttg                          30
```

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 26

```
gtttaaactt aaaattcttc attacactc                           29
```

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 27

```
ggaattttaa gtttaaactg caaatacgga aatgaaatta at            42
```

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 28

```
acatacgcat gcgaattcaa gtattgatat ggtaaatatg g             41
```

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 29

```
ggaattttaa gtttaaacga ggagtaggtt gaatgggta                39
```

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 30

```
acatacgcat gcgaattcct tgcgctaaaa ttatac                   36
```

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 31
ggaattttaa gtttaaacga ataggagaga ttttataatg gc                          42

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 32
acatacgcat gcgaattcac gagtttgtgg cattggacc                              39

<210> SEQ ID NO 33
<211> LENGTH: 114
<212> TYPE: DNA
<213> ORGANISM: Artificial Sequence
<220> FEATURE:
<223> OTHER INFORMATION: Description of Artificial Sequence: Synthetic
      DNA fragment

<400> SEQUENCE: 33
ggtaccgaag tttgatagat gatacattct attaaacttc cttttttat gctctgaaaa        60 aacaatgatt atctacctta ttagtgcaga tagataacca ttgtttatcc cggg            114

<210> SEQ ID NO 34
<211> LENGTH: 2076
<212> TYPE: DNA
<213> ORGANISM: Escherichia coli

<400> SEQUENCE: 34
cccgggtagg acacaatatc cacttgtagt ttataataac gatctcctcc tttccacttt       60
aattcaaatc tatattaaag aatatttcat cttatttaat aagaaaccat atttatataa      120
caacataaaa cgcactaagt tattttattg aacatatatc ttactttatc tatccgacta      180
tttagacgac gggtctggca aacaggttcg ccagtggtaa cctgatatcc ttttagctct      240
gctaaacaaa cactaagccc atttgtaaaa aagttaaat cattgcgata atcttgaata       300
catcgagcag gaatttctcc aataataatg acctcattat ttttcagttg agtatttacg      360
atatttgcac aatatttggg agcatcgtta tatgcccgtg aaagatattc ctgtggtgca      420
taaactttaa aactaagata tggctctaac aattctgttc cagcttttct aaaggcttgc      480
tccagtacaa taggagtaag catccgaaaa tctgctggag tactaacagg gctatagtat      540
aaaccgtact taaacagat tttacaatcc gtcacattcc aaccatataa tccttgttcg       600
caaccatagc gtatcccttc cataactgca ttttgaaatg attgatttaa gtatccaaga      660
gaaaccgagc tctcatactg cattccactt cccaacggaa gcggtgatac agataaacca      720
atggaagccc agaaaggatt tggcggcact tcgatgtgaa tggtatattc tgcatttttt      780
aacggtctct ccatataaat gactgtaggc tcttttagtt ctatctccac atgatacttt      840
tcttgcaaca gtgcactaat cacttccatt tgtactttcc ctaagaaaga agtataatt      900

-continued

| | |
|---|---|
| tcatgtgtcg tagaatccac gtaatatcgt agaagcggat cactatctga gatttccaaa | 960 |
| agggcatcaa gcaacatttc tctctgttca ggtttactcg gttcaacagt tgtttgtagt | 1020 |
| agagggtgcg gattttcaat cttttttctc tgtggcaata gttttgtatc tccaagaaca | 1080 |
| ctatttaact tcaaaaactc attttgcaaa ataacaattt ctccagaata agctctatca | 1140 |
| atcttacata attcaccatt tattgaagta tacatttctg taacttttat tttttctttt | 1200 |
| tctgatactc taaccgaatc tcgtaaatgt agtactccac tataaaggcg tatatatgca | 1260 |
| agacgttgtc ttttttttgt atattcaatt ttgaaaacat ttccgcaaag ttcagacgga | 1320 |
| cctcgatgtg ttgatgaata aaatttatta gtaataactt ctataaggtt atcaatccct | 1380 |
| atattacttt ttgcacttcc atgataaaga gggaacagag aacaattctg aaatcttatg | 1440 |
| ctttcctctt gttcgagttc caatgcttct aatgatttac cggacatata tttctctaaa | 1500 |
| aggtcatcgt ttccctctat taccgtatcc cattgttcag attcggtaaa gttcgtcaca | 1560 |
| cacatattag gatacagttc taccttctgt ttgattacaa tttcggcaga aagtttctct | 1620 |
| ttaatatcct gataaaccgt tgataaatca attccatttt ggtcaatctt attgataaaa | 1680 |
| aagattgtgg gaatccccat tttcctaagt gcatgaaata atatacgagt ttgtgcttgt | 1740 |
| acgaaatctt ttgcagaaat cagtagaatt gccccatcta aaactgataa tgaacgatat | 1800 |
| acttctgcta agaaatccat atgtcctggc gtgtctatga tgttcacctt cgtatttttcc | 1860 |
| cactgaaaag aggttattcc tgtctgaatt gtaattcctc tctgacgttc taaaagcgta | 1920 |
| ttatccgtcc tcgttgtacc tttgtccacg cttcctaatt ctgtaatcgc tccactgtta | 1980 |
| tataataagc tttctgttaa ggtagttttt cctgcatcaa catgagctaa aactccaata | 2040 |
| ttaataattt tcatgtgatt ttcctccatt ggatcc | 2076 |

<210> SEQ ID NO 35
<211> LENGTH: 615
<212> TYPE: DNA
<213> ORGANISM: Escherichia coli

<400> SEQUENCE: 35

| | |
|---|---|
| ggatccttaa gacccacttt cacatttaag ttgttttttct aatccgcata tgatcaattc | 60 |
| aaggccgaat aagaaggctg gctctgcacc ttggtgatca ataattcga tagcttgtcg | 120 |
| taataatggc ggcatactat cagtagtagg tgtttccctt tcttctttag cgacttgatg | 180 |
| ctcttgatct tccaatacgc aacctaaagt aaaatgcccc acagcgctga gtgcatataa | 240 |
| tgcattctct agaaaaacct tgttggcata aaaaggctaa ttgattttcg agagtttcat | 300 |
| actgtttttc tgtaggccgt gtacttttgc tccatcgcga tgacttagta aagcacatct | 360 |
| aaaacttttta gcgttattac gtaaaaaatc ttgccagctt tccccttcta aagggcaaaa | 420 |
| gtgagtatgg tgcctatcta acatctcaat ggctaaggcg tcgagcaaag cccgcttatt | 480 |
| ttttacatgc caatacaatg taggctgctc tacacctagc ttctgggcga gtttacgggt | 540 |
| tgttaaacct tcgattccga cctcattaag cagctctaat gcgctgttaa tcactttact | 600 |
| tttatctaat ctaga | 615 |

<210> SEQ ID NO 36
<211> LENGTH: 680
<212> TYPE: DNA
<213> ORGANISM: Escherichia coli

<400> SEQUENCE: 36

-continued

```
ggatccttaa gacccacttt cacatttaag ttgtttttct aatccgcata tgatcaattc      60
aaggccgaat aagaaggctg gctctgcacc ttggtgatca ataattcga tagcttgtcg     120 taataatggc ggcatactat cagtagtagg tgtttccctt tcttctttag cgacttgatg     180
ctcttgatct tccaatacgc aacctaaagt aaaatgcccc acagcgctga gtgcatataa     240
tgcattctct agaaaaacct tgttggcata aaaaggctaa ttgattttcg agagtttcat     300 actgttttc tgtaggccgt gtacttttgc tccatcgcga tgacttagta aagcacatct      360 aaaacttta gcgttattac gtaaaaaatc ttgccagctt tccccttcta aagggcaaaa      420
gtgagtatgg tgcctatcta acatctcaat ggctaaggcg tcgagcaaag cccgcttatt     480
ttttacatgc caatacaatg taggctgctc tacacctagc ttctgggcga gtttacgggt     540
tgttaaacct tcgattccga cctcattaag cagctctaat gcgctgttaa tcactttact     600
tttatctaat ctagacatca ttaattccta attttgttg acgacactct atcattgata      660
gagttatttg tcaaactagt                                                 680
```

<210> SEQ ID NO 37
<211> LENGTH: 152
<212> TYPE: DNA
<213> ORGANISM: Artificial Sequence
<220> FEATURE:
<223> OTHER INFORMATION: Description of Artificial Sequence: Synthetic
      Oligonucleotides

<400> SEQUENCE: 37

```
tctagacatc attaattcct ccttttgtt gacactctat cattgataga gttatttgtc      60
aaactagttt tttatttgtc gagttcatga aaaactaaaa aaaattgaca ctctatcatt     120
gatagagtat aattaaaata aaaaagctgc ag                                   152
```

<210> SEQ ID NO 38
<211> LENGTH: 876
<212> TYPE: DNA
<213> ORGANISM: Staphylococcus aureus

<400> SEQUENCE: 38

```
ctgcagcgga gggtttattt tgaaaaagtt aatatttta attgtaattg ctttagtttt       60
aagtgcatgt aattcaaaca gttcacatgc caaagagtta aatgatttag aaaaaaaata    120
taatgctcat attggtgttt atgctttaga tactaaaagt ggtaaggaag taaaatttaa    180
ttcagataag agatttgcct atgcttcaac ttcaaaagcg ataaatagtg ctattttgtt    240
agaacaagta ccttataata agttaaataa aaaagtacat attaacaaag atgatatagt    300
tgcttattct cctattttag aaaaatatga ggaaagata tcactttaaa agcacttatt     360
gaggcttcaa tgacatatag tgataataca gcaaacaata aaattataaa agaaatcggt    420
ggaatcaaaa aagttaaaca acgtctaaaa gaactaggag ataaagtaac aaatccagtt    480
agatatgaga tagaattaaa ttactattca ccaaagagca aaaagagatac ttcaacacct    540 gctgctttcg gtaagacttt aaataaactt atcgcaaatg gaaaattaag caaagaaaac    600
aaaaaattct tacttgattt aatgttaaat aataaaagcg gagatacttt aattaaagac    660
ggtgttccaa aagactataa ggttgctgat aaaagtggtc aagcaataac atatgcttct    720
agaaatgatg ttgcttttgt ttatcctaag ggccaatctg aacctattgt tttagtcatt    780
tttacgaata aagacaataa aagtgataag ccaaatgata gttgataag tgaaaccgcc      840 aagagtgtaa tgaaggaatt ttaagaattc gcatgc                              876
```

<210> SEQ ID NO 39
<211> LENGTH: 872
<212> TYPE: DNA
<213> ORGANISM: Staphylococcus aureus

<400> SEQUENCE: 39

```
ctgcagcgga gggtttattt tgaaaaagtt aatattttta attgtaattg ctttagtttt      60
aagtgcatgt aattcaaaca gttcacatgc caaagagtta aatgatttag aaaaaaaata     120
taatgctcat attggtgttt atgctttaga tactaaaagt ggtaaggaag taaaatttaa     180
ttcagataag agatttgcct atgcttcaac ttcaaaagcg ataaatagtg ctattttgtt     240
agaacaagta ccttataata agttaaataa aaaagtacat attaacaaag atgatatagt     300
tgcttattct cctattttag aaaaatatga ggaaagata tcactttaaa agcacttatt     360
gaggcttcaa tgacatatag tgataataca gcaaacaata aaattataaa agaaatcggt     420
ggaatcaaaa aagttaaaca acgtctaaaa gaactaggag ataaagtaac aaatccagtt     480
agatatgaga tagaattaaa ttactattca ccaaagagca aaaagatac ttcaacaccct     540
gctgctttcg gtaagacttt aaataaactt atcgcaaatg gaaaattaag caagaaaaac     600
aaaaaattct tacttgattt aatgttaaat aataaaagcg gagatacttt aattaaagac     660
ggtgttccaa aagactataa ggttgctgat aaaagtggtc aagcaataac atatgcttct     720
agaaatgatg ttgcttttgt ttatcctaag ggccaatctg aacctattgt tttagtcatt     780
tttacgaata aagacaataa aagtgataag ccaaatgata agttgataag tgaaaccgcc     840
aagagtgtaa tgaaggaatt ttaagtttaa ac                                   872
```

<210> SEQ ID NO 40
<211> LENGTH: 330
<212> TYPE: DNA
<213> ORGANISM: Staphylococcus aureus

<400> SEQUENCE: 40

```
cagctctttc agaaatttcg gttatgcaac atcattacgt tcaaacactc aaggtcgcgg      60
tacttacact atgtacttcg atcactatgc tgaagttcca aaatcaatcg ctgaagatat     120
tatcaagaaa aataaaggtg aataatataa cttgttttga ctagctagcc taggttaaaa     180
tacaaggtga gcttaaatgt aagctatcat ctttatagtt tgattttttg gggtgaatgc     240
attataaaag aattgtaaaa ttctttttgc atcgctataa ataatttctc atgatggtga     300
gaaactatca tgagagataa atttggtacc                                      330
```

<210> SEQ ID NO 41
<211> LENGTH: 385
<212> TYPE: DNA
<213> ORGANISM: Staphylococcus aureus

<400> SEQUENCE: 41

```
gtttaaacga ataggagaga ttttataatg gcaaagaaa aattcgatcg ttctaaagaa       60
catgccaatt cggtacttcg gtcacgttga ccatggtaaa acaacattaa cagcaatcgc     120
tactgtatta gcaaaaaatg gtgactcagt tgcacaatca tatgacatga ttgacaacgc     180
tccagaagaa aaagaacgtg gtatcacaat caatacttct cacattgagt accaaactga     240
caaacgtcac tacgctcacg ttgactgccc aggacacgct gactacgtta aaaacatgat     300
cactggtgct gctcaaatgg acggcggtat cttagtagta tctgctgctg acggtccaat     360
gccacaaaact cgtgaattcg catgc                                          385
```

```
<210> SEQ ID NO 42
<211> LENGTH: 379
<212> TYPE: DNA
<213> ORGANISM: Staphylococcus aureus

<400> SEQUENCE: 42
gagctcggtt gcagatggca ttgtcattgg tagcgaaatc gttaagcgat ttaaatctaa      60
cacgcgtgag gaaatcatta aatatttaca atctatccaa caaacattga ataattaagt    120
ttacttgatt taaaaaaatt aggcgaatac tgtttgaaaa agtgaaaaac ggtgaattat    180
aaaattgaat acaatttcaa aaaagtaat atgagcaaac ccaaacgttc atattacttt     240
ttttgaaatt gtattcaaaa atctaaatat tactataaaa gtacgcaa ttaaagcgtt      300
tatgttttag ttttaacatt aactattgta tacttattta gattagattt attattttg    360
acatttgcag agggtacc                                                   379

<210> SEQ ID NO 43
<211> LENGTH: 420
<212> TYPE: DNA
<213> ORGANISM: Staphylococcus aureus

<400> SEQUENCE: 43
gtttaaactg caaatacgga atgaaatta ttaacgaga acaaatagg agtaatgata        60
atgaagttta caatttaac agctaaagag tttggtgcct ttacagatag catgccatac    120
agtcatttca cgcaaactgt tggccactat gagttaaagc ttgctgaagg ttatgaaaca    180
catttagtgg gaataaaaaa caataataac gaggtcattg cagcttgctt acttactgct    240
gtacctgtta tgaaagtgtt caagtatttt tattcaaatc gcggtccagt gattgattat    300
gaaaatcaag aactcgtaca ctttttcttt aatgaattat caaaatatgt taaaaaacat    360
cgttgtctat acctacatat cgatccatat ttaccatatc aatacttgaa ttcgcatgcg    420

<210> SEQ ID NO 44
<211> LENGTH: 290
<212> TYPE: DNA
<213> ORGANISM: Staphylococcus aureus

<400> SEQUENCE: 44
gagctcgggt tcaatattaa ctgaaaaaga attagattaa atattaattt ggaaaactgg     60
aacaaccaaa aagttatatg accgcgtagg tcttaatgaa gagacgctaa gtattttaga    120
tactgaaatc actaaaaaaa caatacctgt aagacctggt agaaatgttg cggtaattat    180
tgaggtcgct gcaatgaact atcgattaaa tatcatgggc attaacactg ccgaagaatt    240
tagtgaaaga ttaaatgaag aaattatcaa gaacagtcat aagaggtacc                290

<210> SEQ ID NO 45
<211> LENGTH: 434
<212> TYPE: DNA
<213> ORGANISM: Staphylococcus aureus

<400> SEQUENCE: 45
gtttaaacgg aggagtaggt tgaatgggta ttgtatttaa ctatatagat cctgtggcat     60
ttaacttagg accactgagt gtacgatggt atggaattat cattgctgtc ggaatattac    120
ttggttactt tgttgcacaa cgtgcactag ttaaagcagg attacataaa gatactttag    180
tagatattat tttttatagt gcactatttg gatttatcgc ggcacgaatc tattttgtga    240
```

-continued

```
ttttccaatg gccatattac gcggaaaatc caagtgaaat tattaaaata tggcatggtg      300
gaatagcaat acatggtggt ttaataggtg gctttattgc tggtgttatt gtatgtaaag      360
gaaaaattta aacccatttc aaattggtga tatcgttgcg ccaagtataa ttttagcgca      420
aggaattcgc atgc                                                       434
```

AUTOREGULATORY SYSTEM FOR VALIDATING MICROBIAL GENES AS POSSIBLE ANTIMICROBIAL TARGETS USING A TETRACYCLINE-CONTROLLABLE ELEMENT

This application claims the benefit of provisional application No. 60/071,640, filed Jan. 16, 1998.

FIELD OF THE INVENTION

Methods for identifying which microbial genes are targets for inhibition by antibiotics. Specifically a tetracycline-regulated system which provides autoregulatory, inducible gene expression in recombinant microbes, such as bacteria, and in animals infected with the microbes is described.

BACKGROUND OF THE INVENTION

The development of widespread antibiotic resistance in microbial pathogens has created an urgent medical need for new antimicrobial agents. Instead of relying on derivatives of existing antimicrobial agents, the pharmaceutical industry is looking for novel microbial processes to target in an attempt to create new classes of compounds (Knowles, D. J. C., *Trends in Microbiol.*, 1997,5:379–383).

Genes essential for maintaining an infection in an animal or essential for growth of the pathogen in vitro are good targets for antibiotic development. Traditionally, "essential genes" have been prioritized as good antimicrobial targets. Essential genes are those required for microbial cell growth in vitro and include such genes as those encoding DNA gyrase, ribosomal subunits, and cell wall biosynthetic enzymes. Many of these proteins and cell components have been identified as being encoded by essential genes because there are classic antimicrobial agents shown to inhibit the products of these genes (quinolones, tetracyclines, and "beta"-lactams respectively). Other essential genes have been identified from the characterization of conditional lethal mutants.

With the availability of whole microbial genome sequences, there are now many previously unknown and uncharacterized genes available which may turn out to be essential. The conventional approach for testing if a gene is essential is to attempt making a construct of that organism where the test gene is deleted or inactivated. If the organism can survive with the gene deleted or inactivated, the gene is not considered essential. For example, see Strandén, A. M., Ehlert, K., Labischinski, H., and Berger-Bachi, B., 1997, *J. Bacteriol.* 179:9–16. However, failure to create a mutant organism with and inactivated or deleted gene does not always mean that the gene is essential. For example, see Okada, K., Minehira, M., Zhu, X., Suzuki, K., Nakagawa, T., Matsuda, H., and Kawamukai, M., 1997, *J. Bacteriol.* 179:3058–3060. This negative proof for a conclusion may not always be valid. There may be other reasons why the gene deletion or inactivation could not be made.

Recently, virulence factors and genes required for pathogenesis have been suggested as novel targets for antimicrobial agents. Two widely read and referenced techniques, signature tagged mutagenesis (STM; Hensel, M., Shea, J. E., Gleeson, C., Jones, M. D., Dalton, E. and Holden, D., 1995, *Science* 269:400–403) and in vivo expression technology (IVET; Mahan, M. J., Tobias, J. W., Slauch, J. M., Hanna, P. C., Collier, R. J., and Mekalanos, J. J., 1995, *PNAS* 92:669–673) allow scientists to quickly identify a number of bacterial genes required for pathogenesis or that are induced during host infection. While these genes represent good targets for developing attenuated strains for vaccines, it is not clear if they represent valid targets for inhibition by antimicrobial agents. The critical distinction in this evaluation of potential gene targets is that antimicrobial agents are used to inhibit microbial pathogens after infections are established. If virulence factors or pathogenicity genes are only required to establish the infection, inhibition of these in an established infection would not clear the infection. If, after stopping the synthesis of specific genes, an established infection is cleared, those specific genes are essential for maintaining the infection. Therefore, it would be advantageous to develop a method for turning off an endogenous gene to test if it is essential for growth. Such a method would facilitate the identification of antimicrobial targets which should speed the development of new classes of antimicrobial compounds.

Many of the ideas concerning such systems have been disclosed, see the definitions, theories and descriptions of PCT application PCT/US96/07937, International Publication Number WO 96/40979, published 19 Dec. 1996 (19.12.96). PCT/US96/07937 is hereby incorporated by reference into this document; however, recombinant sequences and the examples disclosed in PCT/US96/07937 are NOT incorporated here.

Also U.S. Pat. No. 5,464,758 disclose many of the mechanisms of the tetracycline-Responsive Promoters. U.S. Pat. No. 5,464,758, published 7 Nov. 1995 is incorporated in part here, the general definitions, theories, principles, concepts, general information about the tetracycline operator (tetO) sequences is incorporated into this document by reference but the sequences disclosed in U.S. Pat. No. 5,464,758 are NOT incorporated into this document. Here Applicant describes a system that works.

SUMMARY OF THE INVENTION

This invention provides for a process that allows the characterization of a microbial gene or genes, where the gene encodes a gene product; where the gene product is a gene target; where the gene target is important to a microbe's ability to infect or sustain an infection in a mammal, where the microbe is: genetically altered to become a genetically altered microbe, such that the amount of the gene product produced by the genetically altered microbe is regulated and controlled by a Tetracycline-Controllable Element or TCE; where the TCE is a gene regulatory system that controls the expression of the target gene or gene product, through its ability to modulate the function of the gene in response to the microbe's exposure to tetracycline, and where the TCE is comprised of a tetracycline-controllable transcription promoter polynucleotide sequence; where the gene, which may be any gene which encodes a microbial protein, or more generally a microbial gene product, is regulated by the TCE such that the gene produces either greater or lesser amounts of gene product, depending upon whether or not the genetically altered microbe is exposed to tetracycline; where the mammal is a plurality of at least two or more mammals, where the mammals are initially exposed to tetracycline and infected with the genetically altered microbe; followed by: the removal of the tetracycline exposed to a portion of the mammals, such that at least one or some mammals of one group of the mammals are exposed to tetracycline and the other one or group of mammals are not exposed to tetracycline; followed by: a comparison of the degree of infection, microbe levels, or physiological condition of the mammals exposed to tetracycline, compared to the degree of infection, microbe levels, or physiological condition of mammals not exposed to tetracycline; followed by: the identification of the genes, important to a microbe's ability to infect or sustain an infection in a mammal, where the comparison of the mammals exposed to tetracycline compared to the mammals not exposed to tetracycline shows a meaningful difference between the two groups of animals, or the infection levels of those animals.

In related aspects of the invention the TCE is a gene regulatory system that controls the expression of the target gene or gene product, through its ability to modulate the function of the gene in response to the microbe's exposure to tetracycline, and where the TCE is comprised of a tetracycline-controllable transcription promoter polynucleotide sequence, operably linked to a polynucleotide sequence encoding a reporter gene, the tetracycline-controllable transcription promoter polynucleotide sequence, is a prokaryotic transcription promoter, that may be operably linked to a polynucleotide sequence encoding a reporter gene (RG) and a target gene (TG). The reporter gene can be lactamase. The microbe can have additional genetic alterations comprising a tetracycline resistance (or protection) and repressor DNA cassette (TRRDC). The TCE, the TRRDC, the RG, and the TG can all be on the same DNA cassette, which may be referred to as a Regulatory DNA Cassette or RDC, but the other components beyond the TCE are not required to be on the RDC. The TRRDC can comprise the structural gene tetM, a tetracycline resistance gene, the structural gene tetR, a tetracycline repressor gene and it can have a promoter operably linked to the TCE.

A meaningful difference between the two groups of animals being tested is a mathematically significant difference in the survival rates or the levels of microbes, or levels of infection present in the mammals. The meaningful difference between the two groups of animals is a mathematically significant difference in the survival rates of the groups of animals. The significant difference in the survival rates of the groups of animals shows that animals exposed to tetracycline have poorer health, higher rates of infection, lower survival or higher levels of microbes than animals not exposed to tetracycline. The animals can be mammals, preferably mice or other rodents.

The tetracycline resistent gene of the TRRDC can be comprised of sequences from the *Staphylococcus aureus* tetM gene. The tetracycline repressor gene of the TRRDC can be derived from the Tn10 transposon.

The microbe can be a recombinant bacterium. It can be a *Staphylococcus* species, such as *Staphylococcus aureus*, or a virus, a lower eukaryote, or even a yeast.

The invention further comprises an isolated DNA molecule for integrating a heterologous polynucleotide sequence at a pre-determined location in a prokaryotic chromosome to operably control an endogenous prokaryotic gene, the DNA molecule comprising recombining element (RE) and a tetracycline controllable element (TCE), the TCE comprising a tetracycline-controllable prokaryotic transcription promoter polynucleotide sequence flanked at its 5' end by the RE, the RE comprising additional polynucleotide sequences of sufficient length for homologous recombination between the isolated DNA molecule and the prokaryotic chromosome.

This isolated DNA molecule can have a polynucleotide sequence encoding a reporter gene operably linked to the TCE. The reporter gene can be beta-lactamase. In some cases at least one prokaryotic transcription terminator polynucleotide sequence is positioned between the RE and the TCE. The DNA can also have a polynucleotide sequence encoding a prokaryotic tetracycline resistance protein operably linked to a prokaryotic transcription promoter polynucleotide sequence positioned between the RE and the TCE. The tetracycline resistance protein can be derived from the *Staphylococcus aureus* tetM gene. The DNA can have a polynucleotide sequence encoding a prokaryotic tetracycline repressor protein operably linked to a tetracycline-controllable prokaryotic transcription promoter polynucleotide sequence positioned between the RE and the TCE. The tetracycline repressor may be a Tn10 transposon, derived from a Tet repressor. Sequences of Tn10 transposons are disclosed herein. Associated vectors and cells, especially prokaryotic host cells, are described. The DNA has various recombining elements and tetracycline-controllable elements, reporter genes like beta-lactamase whose sequences may be selected from the sequence listing.

The DNA molecules herein can be operably inked to a reporter gene, such as beta-lactamase (β-lactamase), especially a beta-lactamase from the included sequence listing, and the reporter gene can be operably linked to the tetracycline-controllable element.

The tetracycline resistance protein can be derived from the *Staphylococcus aureus* tetM gene or from various sequences provided. The tetracycline repressor may be a tetR gene derived from the Tn10 transposon, and several sequences are provided. At least on prokaryotic transcription terminator sequence can be positioned between the tetracycline-controllable element and one or more recombining elements. A prokaryotic tetracycline resistance protein can be operably linked to a transcription promoter polynucleotide sequence. A polynucleotide sequence encoding a tetracycline repressor protein can be operably linked to a transcription promoter polynucleotide sequence. The DNA described here can be made into a form suitable for transformation of a host cell.

The invention further comprises another different type of isolated DNA molecule for integrating a heterologous polynucleotide sequence at a pre-determined location in a prokaryotic cell. This other type of DNA can be described as an isolated DNA molecule for integrating a polynucleotide sequence including tetracycline-controllable elements (TCE) at a pre-determined location in a target DNA molecule, the isolated DNA molecule comprising the following DNA elements fused in sequence: a) a first prokaryotic transcription terminator polynucleotide sequence; b) a second prokaryotic transcription terminator polynucleotide sequence; c) a polynucleotide sequence encoding a prokaryotic tetracycline resistance protein; d) a polynucleotide sequence encoding a prokaryotic repressor protein; e) a first tetracycline-controllable prokaryotic transcription promoter polynucleotide sequence; f) a second tetracycline-controllable prokaryotic transcription promoter polynucleotide sequence; and g) a polynucleotide sequence encoding a reporter protein; the isolated DNA molecule comprising a polynucleotide sequence including the TCE flanked at the end opposite the polynucleotide sequence encoding the reporter protein by additional polynucleotide sequences of sufficient length for homologous recombination between the isolated DNA molecule and the target DNA molecule at a pre-determined location. All of the modifications described above can be applied to the DNA molecule described in this paragraph. This DNA molecule may also be described as a DNA cassette, it may also be called an RDC. Note an RDC does not have to be on a single cassette, the elements of an RDC can be fashioned in many different ways. Elements of the RDC can even be taken from the microbe itself.

Finally, this system is described in detail with bacterial organisms, but it can also be adapted to other types of organisms. When the system is used with a virus, eukaryote or yeast, the transcription promoters and structural genes should be modified in a manner apparent to one skilled in the art that would make the promoters and genes active in that organism.

BRIEF DESCRIPTION OF THE FIGURES

FIG. 1 shows three linked DNA cassettes or elements. The three components shown, which may be operably linked but need not be, are a TRRDC, (Tetracycline Resistance (or protection) and Repressor DNA Cassette); a TCE (Tetracycline-Controllable Element); and RG (Reporter Gene), together the components, which need not be linked are called the RDC (Regulatory DNA Cassette). Arrowheads represent transcription start sites and the direction of transcription. The two octagons represent transcription terminators. Boxes represent coding regions for the genes, the arrows show the direction of transcription of these genes. The open circles represent tetO sequences, where tetracycline-repressor protein binds in the absence of tetracycline. Vertical bars represent restriction endonuclease cleavage sites. The region between the cleavage sites between the tetR and BlaZ coding regions is the TCE region. The tetM, tetR, TCE and BlaZ are described herein. FIG. 1 shows a particular embodiment of this invention because it shows three transcription promoter systems, the TCE, the TRRDC and the RG combined in a single DNA element where in fact, neither the TRRDC nor the RG must be in the same DNA construct as the TCE.

FIG. 2, SEQ. ID. NO. 33, is the nucleotide sequence of the synthetic DNA fragment of the regulatory cassette containing two transcription terminator sequences. The nucleotides in bold letters comprise recognition sequences for the restriction endonuclease indicated above in italics. The dotted arrows indicate the regions of dyad symmetry of the rho-independent terminator sequences where putative stem-loops form followed by a string of T's during transcription.

FIG. 3, SEQ. ID. NO. 34, is the nucleotide sequence of the amplified DNA fragment for the element of the regulatory cassette encoding tetracycline resistance gene, the tetM. The nucleotides in bold letters comprise recognition sequences for the restriction endonucleases indicated above in italics. The DNA represents the coding strand for the gene, with transcription and translation occurring from top to bottom as shown in this Figure.

FIG. 4a, SEQ. ID. NO. 35, is the nucleotide sequence of the amplified DNA sequence for the element. The nucleotides in bold letters comprise recognition sequences for the restriction endonucleases indicated above in italics. The DNA represents the coding strand for the gene, with transcription and translation occurring from top to bottom as shown in this figure.

FIG. 4b, SEQ. ID. NO. 36, is the nucleotide sequence of FIG. 4a with additional sequence from the 5' untranslated region of the tetR gene. The nucleotides in bold letters comprise recognition sequences for the restriction endonucleases indicated above in italics. The DNA represents the coding strand for the gene, with transcription and translation occurring from top to bottom as shown in this figure.

FIG. 5, SEQ. ID. NO. 37, is the nucleotide sequence of the synthetic DNA fragment of the regulatory cassette containing two diverging transcriptional promoters with tetO sequences. The nucleotides in bold letters comprise recognition sequences for the restriction endonucleases indicated above in italics. Capitalized nucleotides on both DNA strands represent tetO sequences, putative binding sites for the tet repressor protein in the absence of tetracycline. The −35 and −10 regions of the tet promoter ($P_{tet}$) and xyl promoter ($P_{xyl}$) are underlined and overlined, respectively. The capitalized ATG on the bottom strand indicates the start codon of the tetR open reading frame.

FIG. 6a, (SEQ. ID. NO. 38) and FIG. 6b (SEQ. ID. NO. 39) are the nucleotide sequences of alternative amplified DNA elements for the regulatory cassette encoding the reporter gene, BlaZ. The nucleotides in bold letters comprise recognition sequences for the restriction endonucleases indicated above in italics. The DNA represents the non-coding strand of the DNA, with transcription and translation going from top to bottom in this figure. FIG. 6a (SEQ. ID. NO. 38) represents the sequence which would be used for constructs where the cassette could be integrated into the chromosome. FIG. 6b (SEQ. ID. NO. 39) represents the sequence which would be used for constructs where the reporter gene is cloned downstream of the target gene.

FIG. 7a, SEQ. ID. NO. 40, is the nucleotide sequence of the amplified DNA homologous to *Staphylococcus aureus* chromosomal DNA upstream to the endogenous structural gene for elongation factor Tu (EF-Tu). FIG. 7b, SEQ. ID. NO. 41, is the nucleotide sequence of the amplified DNA homologous to *Staphylococcus aureus* chromosomal DNA overlapping the 5' end of the structural gene for EF-Tu. The nucleotides in bold letters comprise recognition sequences for the restriction endonucleases indicated above in italics.

FIG. 8a, SEQ. ID. NO. 42, is the nucleotide sequence of the amplified DNA homologous to *Staphylococcus aureus* chromosomal DNA upstream to the endogenous structural gene for femA. FIG. 8b, SEQ. ID. NO. 43, is the nucleotide sequence of the amplified DNA homologous to *Staphylococcus aureus* chromosomal DNA overlapping the 5' end of the structural gene for femA. The nucleotides in bold letters comprise recognition sequences for the restriction endonucleases indicated above in italics.

FIG. 9a, SEQ. ID. NO. 44, is the nucleotide sequence of the amplified DNA homologous to *Staphylococcus aureus* chromosomal DNA upstream to the endogenous structural gene for lgt. FIG. 9b, SEQ. ID. NO. 45, is the nucleotide sequence of the amplified DNA homologous to *Staphylococcus aureus* chromosomal DNA overlapping the 5' end of the structural gene for lgt. The nucleotides in bold letters comprise recognition sequences for the restriction endonucleases indicated above in italics.

DETAILED DESCRIPTION OF THE INVENTION

Figure 1:
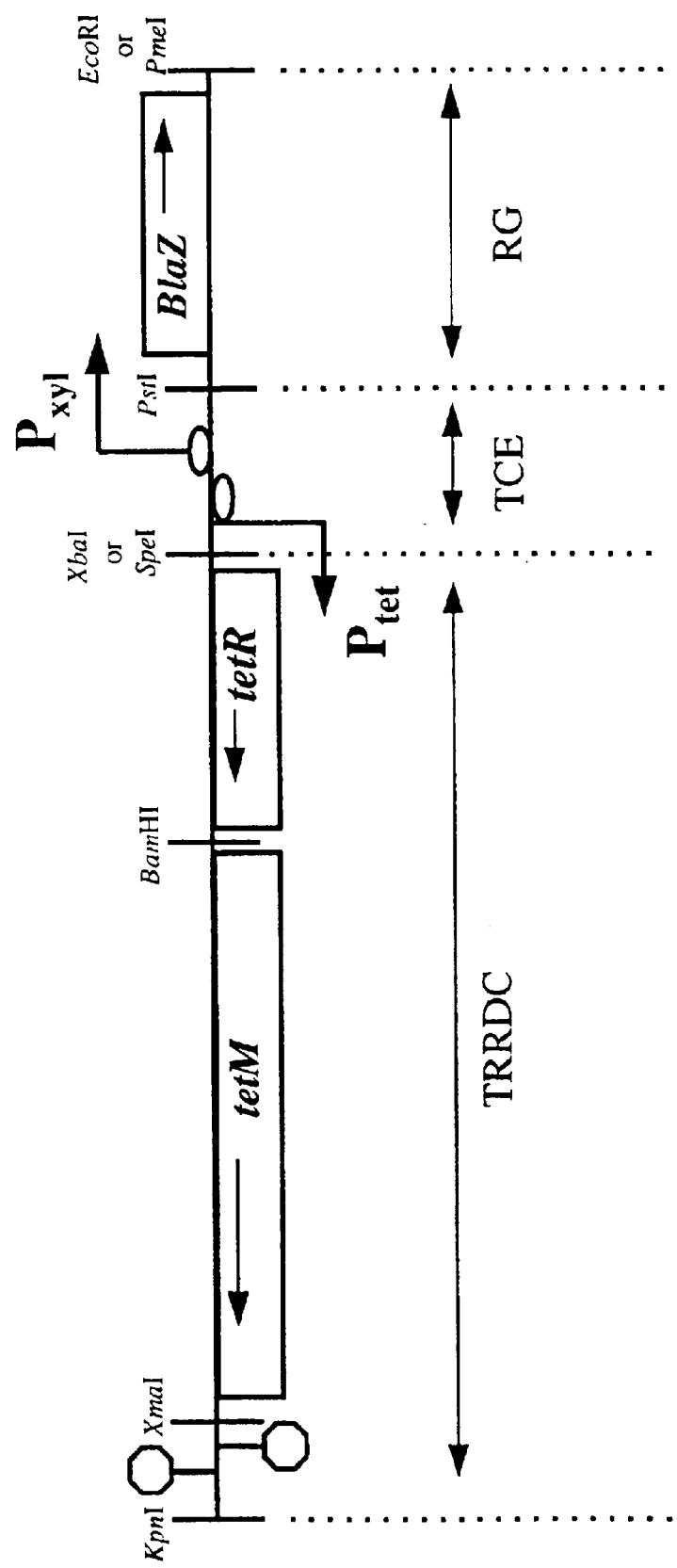
FIG. 1 is a schematic representation of a preferred embodiment of the invention.

Definitions. Throughout this document words and phrases are used that should be known to one skilled in the art. A PhD scientist having experience in the field will know what is described here. The documents incorporated by reference define many terms. In some cases special words, phrases or abbreviations are used that are unique to this document. The meaning of those special or unique words, phrases or abbreviations can be learned either from reading them in context and/or they are described immediately below.

C when followed by a number refers to temperature in degrees celsius. The C may be followed by a slash"/" and a number, or the C may be followed by a superscript "°" and a number, e.g. C/37 or C°37.

Beta-lactamase or β-lactamase is a reporter gene and protein. It is further described below.

gene product—means any protein, enzyme, nucleic acid, ribosome components, compounds, even sugar coded by or directly resulting from a protein whose sequence was coded for by the subject gene.

RDC—means a stable Regulatory DNA Cassette, it is further described below.

RE—means Recombining Elements, it is further described below.

TCE—means a Tetracycline-Controllable Element, it is further described below.

TRRDC—means a Tetracycline Resistance (or protection) and Repressor DNA Cassette (TRRDC), it is further described below.

RG—means reporter gene, it may also be called a marker gene or enzyme. Sometimes when read in context reporter gene will refer to the reporter protein.

tetO—means tetracycline operator sequences, it is further described below.

micron—can be abbreviated with the symbol "u" or "$\mu$."

Tn10—means means a bacterial transposon that can confer tetracycline resistance in E. coli and other entarobacteria, it is further described below.

Here we describe a way to identify which microbial genes are essential for maintaining an infection. We disclose a screen designed to genetically engineer microbial pathogens so that expression of specific genes can be regulated in vitro and during host infection. To accomplish this, heterologous DNA sequences are inserted into the bacterial chromosome to disrupt wild type expression of a targeted gene. Expression of the targeted gene is then regulated by inserting a regulatory cassette into the chromosome such that the regulatory cassette controls expression of the targeted gene. Alternately the targeted gene can be cloned and put under the control of a regulatory cassette somewhere else in the chromosome or on an extrachromosomal DNA fragment. This theory can be applied to any gene regulatory system where the gene is regulated and controlled by regulatory elements and where the regulatory elements respond to exogenous influences. Examples exist of regulatory elements controlled or influenced by such things as for example, beta-lactamase, beta-galactoside and nutritional factors such as sugars, (glucose, etc.), amino acids, (tryptophan, etc,) and chemical elements, (iron, etc.).

Applicant's incorporate the definitions, theories and descriptions of PCT application PCT/US96/07937, International Publication Number WO 96/40979, published 19 Dec. 1996 (19.12.96), in part, into this document by reference. Recombinant sequences and the examples disclosed in PCT/US96/07937 are NOT incorporated into this document.

U.S. Pat. No. 5,464,758, published 7 Nov. 1995 is incorporated in part here, the general definitions, theories, principles, concepts, general information about the tet operator (tetO) sequences is incorporated into this document by reference but the sequences disclosed in U.S. Pat. No. 5,464,758 are NOT incorporated into this document.

Here we specifically describe gene regulatory elements which respond to the presence or absence of tetracycline. Tetracycline is thus used to regulate the expression of the targeted genes. Because tetracycline is not normally present in animals, a tetracycline-regulated microbial gene can be controlled in vivo by adding or removing tetracycline from the infected animals' diet.

This invention describes a method for evaluating microbial gene products as targets for antimicrobial agents. Antibiotics work by targeting a microbial process essential for survival of the microbe in the infected host. By genetically engineering microbes so that genes can be shut off while the microbes are infecting a mammal it allows us to mimic the effect of a compound that inhibits a process where the gene product is involved. If the gene product is required by the microbe for survival in the host, turning off the gene is comparable to treating the infection by administering antibiotics that target any process in which that gene is involved. In this way, we can test the effect of inhibiting these steps without having to first screen for specific chemical inhibitors.

PCT publication, WO 96/40979, assigned to Microcide Pharmaceuticals, Inc. suggests it might be possible to regulate the genes of a microbe during an infection, but the document does not describe how this could be done. The description provided in this document now describes a method for genetically engineering a microbe so that a specific gene of interest in the microbe can be regulated while the microbe is infecting a mammal. This genetically engineered system for regulating genes of interest is controlled by the presence or absence of tetracycline. In this invention, a mammal could be infected with the genetically engineered microbe while feeding the mammal tetracycline. The system is designed such that the gene is expressed in the presence of tetracycline. Once the infection is established, tetracycline is removed from the diet, turning off expression of the gene. If the target is a gene or gene product required for the infection, removing the tetracycline and turning off the gene should clear the infection from the mammal.

Genetic engineering of the microorganism requires the incorporation of a TCE into the microbe. TCE means a Tetracycline-Controllable Element, and it is more fully described below.

The TCE can be made into part of a defined DNA unit or DNA cassette, which can contain about 5 or 6 different elements. These elements are all shown as part of FIG. 1. Those elements can include: a) 1 to several transcription terminators; b) the structural gene tetM, c) the structural gene tetR; d) 1 to several promoters; e) a reporter element or reporter gene, which is here exemplified by the structural gene for BlaZ. f) These different elements have restriction sites which allow compatible ends and this allows for ligation of the different elements into the DNA cassette. The entire DNA cassette shown in FIG. 1 is called the Regulatory DNA Cassette or the RDC.

Note, the structural gene tetM, and the structural gene tetR do not need to be part of the RDC per se, rather they can be on a different plasmid or otherwise inserted into the microbe in a manner where they are expressed by the microbe, but they do not need to be controlled by the promoters in the RDC. The structural gene tetM, the structural gene tetR and a promoter sequence are referred to here as the tetracycline resistance (or protection) and repressor DNA cassette (TRRDC). As is used in this document, the tetracycline repressor gene refers to the structural gene tetR and its associated protein, the tetracycline repressor protein refers to the structural protein TetR. As is used in this document, the tetracycline resistance gene refers to the structural gene tetM and its associated protein, the tetracycline resistance protein refers to the structural protein, TetM. The function, purpose and design of the tetR and tetM genes and gene products are more fully discussed below. The components of the TRRDC are shown in FIG. 1. The three elements, the TRRDC, the TCE and the Reporter Gene (RG), are all shown in FIG. 1.

The transcription terminators also are not required in the TRRDC but they may be in the TRRDC, as is shown in FIG. 1. The reporter gene, RG, can be any gene which expresses a gene product which can be quantitatively assayed. Here we have found the BlaZ gene makes a preferred reporter gene. Thus, FIG. 1 is shown to be a particular embodiment of this invention. FIG. 1 shows two transcription promoter systems in a single DNA element or cassette where in fact they do not need to be combined in this manner. What is required is that the target gene and the reporter gene both be controlled by the same promoter system, and this system is regulated by tetracycline. The structural genes for the structural gene tetM, and the structural gene tetR can be controlled by a promotor or promoters from any source that functions in the microbe, such as a separate plasmid.

The key component of the RDC, is the TCE (tetracycline-controllable element) which is a gene regulatory system that controls the expression of the target gene, or gene product. The target, or gene product being evaluated as a target for antimicrobial treatment is controlled by a transcription promoter that in turn is regulated by a tetracycline repressor protein encoded by tetR. In the absence of tetracycline, the tetR-encoded protein binds tetracycline operator sequences (tetO) around the transcription promoter, reducing or preventing transcription from the promoter. In the presence of tetracycline, the tetR-encoded protein binds tetracycline, preventing binding to the tetO sequences, allowing transcription from the promoter. (TCE) has the promoter sequences allowing for transcription of the target gene and includes tetO sequences. In this example we have included the tetR gene in the RDC, but it could be incorporated into the microbe as a separate component, either as a chromsomal insertion or on a plasmid vector.

The tetracycline-controllable element (TCE) system in the example shown here is based on regulatory elements of a tetracycline-resistance operon. Tn10 is a transposon with a tetracycline-regulatory system. Tn10 is described in Hillen & Wissmann, "Tet repressor-tet operator interaction," in *Protein-Nucleic Acid Interaction*, Saeger and Heinemann, eds., Macmillan, London, 1989, Vol. 10, pp. 143–162), incorporated by reference into this document. Transcription of resistance-mediating genes within Tn10 is negatively regulated by a tetracycline repressor (TetR). In the presence of tetracycline or a tetracycline analogue, TetR does not bind to its operators located within the promoter region of the operon, allowing transcription. Promoters operably fused to tetracycline operator (tetO) sequences are virtually silent in the presence of TetR and low concentrations of tetracycline.

The specificity of the Tet R for its operator sequence (Hillen & Wissmann, "Tet repressor-tet operator interaction," in *Protein-Nucleic Acid Interaction*, Saeger & Heinemann, eds., Macmillan, London, 1989, Vol. 10, pp.143–162) as well as the high affinity of tetracycline for TetR (Takahashi et al., *J. Mol. Biol.*, 187:341–348 (1986)) and the well-studied chemical and physiological properties of tetracyclines constitute a basis for an inducible expression system in prokaryotic cells.

The present invention also relates to a second polynucleotide molecule coding for a protein, wherein said polynucleotide is operably linked to a minimal promoter operatively linked to at least one tet operator (tetO) sequence. The tetO sequence may be obtained, for example according to Hillen & Wissmann, "Topics in Molecular and Structural Biology," in *Protein-Nucleic Acid Interaction*, Saeger & Heinemann, eds., Macmillan, London, 1989, Vol. 10, pp. 143–162, the contents of which are fully incorporated by reference herein. Other tetO sequences which may be used in the practice of the invention may be obtained from the references given in the following: Waters et al., *Nucl. Acids Res.* 11:6089–6105 (1983); Postle et al., *Nucl. Acids Res.* 12:4849–4863 (1984); Unger et al., *Gene* 31:103–108 (1984); Unger et al., *Nucl. Acids Res.* 12:7693–7703 (1984); Tovar et al., *Mol. Gen. Genet.* 215:76–80 (1988); for comparison and overview see Hillen & Wissmann in *Protein-Nucleic Acid Interaction*, Saeger & Heinemann, eds., Macmillan, London, 1989, Vol. 10, pp. 143–162 and can also be utilized for the expression system described. All references in this paragraph incorporated by reference into this document.

To prevent killing of the microbe by the tetracycline used to regulate the system, a gene encoding a protein that confers tetracycline resistance is also added to the construct. Tetracyline functions as an antibiotic by interfering with an elongation factor required for protein synthesis. Some genes conferring tetracycline resistance express a gene product that would effect the tetracycline levels in the cell, either by pumping tetracycline out of the cells, or by chemically altering the tetracycline. Because tetracycline is needed to regulate the TCE, it is important to use a tetracycline resistance gene that does not alter the tetracycline levels in the microbe. Specifically, the tetM gene, a tetracycline resistance gene, was chosen to provide tetracycline protection to the microbe. The tetM gene encodes a protein believed to be an alternative ribosomal elongation factor that can function in the presence of tetracycline. Here we describe adding the tetM gene to make the RDC, but it too could be added seperately to the microbe, by insertion into the chromsome or on a plasmid vector.

In addition, a reporter gene may be added to the construct that allows for an easy way to measure the amounts of protein expressed from a gene under control of the RDC. Alternatively the reporter gene may be present in the microbe. In our case, the gene BlaZ, encoding β-lactamase is used as the reporter gene. This gene allows for selection of expression in that it confers resistance to β-lactams. That is, organisms expressing this gene can be selected by their survival in the presence of β-lactams. Furthermore, the levels of β-lactamase can be quantitatively assayed by a simple calorimetric assay. By following the levels of β-lactamase activity in the presence or absence of tetracycline, we can measure the sensitivity of the TCE, using this to select optimized TCE sequences.

The TCE must then be linked to the target genes in the microbe. This can be accomplished in several ways. Here two promenent methods will be discussed as Option I and Option II. Other options should be apparent to one ordinarily skilled in the art.

Option I. The TCE alone; the TCE ligated to tetR, tetM and BlaZ; or the full RDC, can be inserted into the chromosome. Recombining elements (RE) flanking the inserted DNA should be designed to have enough sequence identity with the host chromosomal DNA to allow homologous recombination into the chromosome. The RE sequences are designed to target insertion so that the cassette is between the target gene and its endogenous transcription promoter sequences. In this way, the natural controlling sequences are removed from the target gene, and the target gene expression is controlled by the TCE as inserted or the TCE as part of the RDC.

Option II. Another method for linking the target genes to the TCE involves introduction of the target gene between the TCE (either alone; or ligated to tetR, tetM and BlaZ; or as part of the RDC) and the reporter gene or just after the reporter gene on a plasmid vector in the microbe. In this Option II method, a microbe is used which has the wildtype target gene from the chromosome inactivated. The target gene is then ligated into the TCE containing DNA fragment and inserted into a suitable plasmid vector for stable transformation of the microbe.

The genetically engineered microbe is then used to infect a sample of mammals such as mice. For example, two groups of mice, say Group A mice and Group B mice, are all treated with tetracycline (possibly by adding tetracycline to their drinking water) while being infected with the microbe. In both groups of mice, the gene in the infecting microbe should be on and producing functional product because the microbe is exposed to tetracycline being fed to the animals. Tetracycline is then removed from the water of the Group B mice. The Group A and Group B mice are then compared over time. Because the Group A mice are still exposed to tetracycline, the target gene in the microbe should be on and functioning in Group A infections. But in the Group B mice, expression of the target gene in the infecting microbe should be reduced, or even turned off, once the tetracycline is removed. If the Group A mice, the mice with microbes having a functioning gene, continue to show signs of infection and continue to get sick and possibly even die, while at the same time the Group B mice, infected with microbes where the gene is turned off, and thus producing less gene product, may be able to recover from the infection, or they may show signs of improvement, or if they at least don't die, then one knows that the controlled gene or gene product is important for the microbe to sustain the infection and should be selected as an antimicrobial target. This type of difference would be considered a significant difference. Any significant difference would also be considered a meaningful difference between the two groups of animals. Significance can also be quantified with well known statistical tests. A meaningful difference could be determined by one ordinarily skilled in the art of evaluating microbial infections.

If both Group A and B mice continue to get sick or continue to suffer from the microbial infection, after tetracycline is removed from the diet of Group B mice, that indicates the gene is probably not a good target for further antimicrobial research, because inhibiting the protein or gene product probably will not cure the infection in a mammal anyway.

This is just one example of how the system may be used, obvious variations of the above example should be apparent to one skilled in the art. The invention being described above, the authors would now like to provide a few preferred embodiments of the invention.

Preferred Embodiments

A preferred embodiment of the invention relates to an isolated DNA molecule, or DNA cassette, for integrating a heterologous polynucleotide sequence at a pre-determined location in a microbial chromosome to operably control an endogenous prokaryotic gene or as an extrachromosomal element cloned such that it operably controls a functional copy of the targeted gene, the DNA molecule comprising a tetracycline controllable element (TCE) where the TCE comprises a tetracycline-controllable prokaryotic transcription promoter. For integration into the microbial chromosome, the TCE polynucleotide sequence is flanked at its 5' end, and optionally and the 3' end, by a recombining element (RE), where the RE comprises additional polynucleotide sequences of sufficient length for homologous recombination between the isolated DNA molecule and the microbial chromosome.

In a preferred embodiment, the isolated DNA molecule referred to above further comprises a polynucleotide sequence, which encodes a reporter gene, that is operably linked to the TCE. The reporter gene can be a fluorescent marker, an enzyme such as beta-galactosidase, a protease, here the preferred reporter gene is beta-lactamase.

In an alternative preferred embodiment, the isolated DNA molecule referred to above further comprises at least one transcription terminator polynucleotide sequence positioned between the RE and the TCE.

In yet another preferred embodiment, the isolated DNA molecule referred to above further comprises a polynucleotide sequence, which encodes a prokaryotic tetracycline resistance protein, operably linked to a transcription promoter polynucleotide sequence positioned between the RE and the TCE. Preferably, the tetracycline resistance protein is derived from the *Staphylococcus aureus* tetM gene.

In another preferred embodiment, the isolated DNA molecule referred to above further comprises a polynucleotide sequence, which encodes a prokaryotic tetracycline repressor protein, operably linked to a tetracycline-controllable prokaryotic transcription promoter polynucleotide sequence positioned between the RE and the TCE. Preferably, the tetracycline repressor is derived from the transposon Tn10, see Postle, K., Nguyen, T. T., and Bertrans, K. P., 1984, *Nucleic Acids Research* 12:4849–4863, incorporated into this document by reference.

In an alternative preferred embodiment, the isolated DNA molecule referred to above is a recombinant vector in a form suitable for transformation of a host cell. Another preferred embodiment comprises a host cell transformed with this recombinant vector.

Another preferred embodiment comprises a microbial host cell comprising the DNA molecule referred to above wherein the DNA molecule is integrated at a pre-determined location in the host cell chromosome.

An alternative preferred embodiment of the invention relates to an isolated DNA molecule for integrating a polynucleotide sequence including tetracycline-controllable elements (TCE) at a pre determined location in a target DNA molecule, the isolated DNA molecule comprising the following DNA elements fused in sequence: a first transcription terminator polynucleotide sequence; a second transcription terminator polynucleotide sequence, a polynucleotide sequence encoding a prokaryotic tetracycline resistance protein; a polynucleotide sequence encoding a prokaryotic repressor protein; a first tetracycline-controllable transcription promoter polynucleotide sequence, a second tetracycline-controllable transcription promoter polynucleotide sequence, and a polynucleotide sequence encoding a reporter protein; the isolated DNA molecule comprising a polynucleotide sequence including the TCE flanked at the end opposite the polynucleotide sequence encoding the reporter by additional polynucleotide sequences of sufficient length for homologous recombination between the isolated DNA molecule and the target DNA molecule at a pre-determined location. In a preferred embodiment, a recombinant vector comprising the isolated DNA molecule is in a form suitable for transformation of a host cell. In a further embodiment, this isolated DNA molecule is integrated at a predetermined location in a microbial host cell chromosome.

In an alternative preferred embodiment, the DNA relates to a recombinant vector suitable for the transformation of the microbial pathogen containing the following items: a polynucleotide sequence encoding a prokaryotic tetracycline resistance protein; a polynucleotide sequence encoding a prokaryotic repressor protein; a first tetracycline-controllable transcription promoter polynucleotide sequence; with the following in sequence: a second tetracycline-controllable transcription promoter polynucleotide sequence an isolated DNA molecule comprising a polynucleotide sequence encoding the targeted gene; and a polynucleotide sequence encoding a reporter protein.

A preferred embodiment is a DNA cassette as shown in FIG. 1 and as the components of FIG. 1 are described in this document.

The above descriptions should completely describe the invention and the examples below, both synthesis examples and working models are provided to illustrate but not limit the above descriptions of the invention.

EXAMPLES

Materials and Methods
Construction of Tetracycline-responsive DNA Regulatory Cassette:

A DNA cassette is constructed for introduction into *S. aureus* either by homologous recombination into the *S. aureus* chromosome at a specific site by Campbell-type recombination, see Campbell, A., 1962, *Advan. Genet.*, 11:101–145, incorporated into this document by reference, or on an autonomously replicating plasmid. For chromosomal integration, this DNA contains a region at one or both ends homologous to regions of the *S. aureus* chromosomal DNA. The rest of the construct contains a recombinant DNA cassette as illustrated in FIG. 1. On an autonomously regulated plasmid, the recombinant DNA cassette in FIG. 1 would contain DNA encoding a *S. aureus* gene.

The first element of this cassette contains two transcription terminators, which are designed to prevent transcriptional read-through from the chromosomal DNA into this insert as well as transcriptional read-through from the cassette into the chromosome. These are followed by a *S. aureus* gene conferring resistance to tetracycline, tetM. This gene was chosen because the mechanism of resistance does not appear to change the structure or concentration of tetracycline in the cell, rather it appears to provide an alternative elongation factor which is resistant to the tetracycline in translation, see Nesin, M., Svec, P., Lupski, J. R., Godson, G. N., Kreiswirth, B., Kornblum, J. and Projan, S. J., *Antimicrob. Agents Chemother.*, 1990, 34:2273–2276, incorporated into this document by reference. This gene is transcribed from left to right as shown in FIG. 1. Alternatively, tetM could be incorporated somewhere else in the chromosome of *S. aureus* to provide a background strain useful for a number of targeted gene tests. The gene encoding *E. coli* tet repressor, tetR, see Postle, K., Nguyen, T. T., and Bertrand, K. P., *Nuc. Acids Res.*, 1984, 12:4849–4863, incorporated into this document by reference, is transcribed as an operon with tetM from an adjacent promoter on the region containing two diverging promoters ($P_{tet}$ and $P_{xyl}$) and two tetracycline operator sequences (tetO). The tet repressor protein binds tetO sequences in the absence of tetracycline, preventing transcription from $P_{xyl}$. In the presence of tetracycline, tet repressor binds tetracycline and not tetO sequences, allowing transcription from $P_{xyl}$. The strong *B. subtilis* promoter, $P_{xyl}$, signals initiation of transcription to the right as drawn in FIG. 1, allowing transcription of *S. aureus* BlaZ encoding beta-lactamase, an assayable marker gene which confers resistance to ampicillin, see Wang, P. Z. and Novick, R. P., 1987, *J. Bacteriol.*, 169:1763–1766, incorporated into this document by reference. When this DNA is inserted into the chromosome, the gene being tested as target should be transcribed in an operon with BlaZ, and have similar transcriptional regulation. When the DNA is contained on an autonomously regulated plasmid, the DNA encoding the target gene would be inserted next to BlaZ so that the target gene and BlaZ should be transcribed in a single operon and have similar regulation.

The following paragraphs describe how each of the DNA cassette elements are made. For totally synthetic elements (1 and 4), DNA oligonucleotides are designed to leave overhanging nucleotides at both ends that resemble the sticky ends left by digestion with restriction endonucleases. For elements amplified by PCR, oligonucleotides are designed to incorporate unique recognition sites for restriction endonucleases on both ends. These restriction sites simplify ligations with each other and with restriction enzyme digested plasmids. Oligonucleotides were synthesized by Genosys Biotechnologies, Inc., The Woodlands, Tex.

DNA ligations are performed in T4-DNA ligation buffer (50 mM Tris HCl, pH 7.6, 10 mM MgCl2, 10 mM dithiothreitol, 50 ug/ml bovine serum albumin) with T4-DNA ligase (Boehringer Mannheim Biochemicals, Indianapolis, Ind.) at 14/C overnight. In general, PCR reactions are carried out in 50 ul reaction volumes using Taq polymerase and reaction buffer from Perkin-Elmer (produced by Roche Molecular Systems, Inc., Branchburg, N.J.). PCR reactions contained 40 uM each of DATP, dCTP, dGTP, and dTTP; 200 nM of each primer; and 1–100 ng chromosomal DNA or plasmid DNA. PCR reactions are heated at 95/C for 5 minutes to denature template, followed by 30 cycles of heating at 95/C for 1 minute, primer annealing at 50/C for 1 minute and elongation at 72/C for 1 minute.

Construction of Element 1: Terminators.

The sequence for the bidirectional terminators are derived from published *S. aureus* transcriptional terminators for sarA (Bayer et al., *J. Bacteriol.*, 1996, 178:4563–4570) and for pcrB (Iordanescu, S., *Mol Gen. Genet.*, 1993, 241:185–192). This element was constructed from four oligonucleotides listed in Table 1 as CLQ459, CLQ460, CLQ461 and CLQ462. Before annealing, 5 pmoles of CLQ460 and CLQ461 were treated at 37/C for 30 minutes with T4-polynucleotide kinase (New England Biolabs, Beverly, Mass.) in 2 mM ATP, 100 mM Tris HCl, pH 7.6, 200 mM spermidine, 10 mM DTT. The reaction was stopped by heating to 85/C for 20 minutes. The kinased CLQ460 and CLQ461 were then mixed with equimolar amounts of CLQ462 and CLQ463, respectively, before heating to 90/C for 5 minutes, followed by cooling to room temperature over 30 minutes. The two pairs of annealed primers were then mixed in equimolar amounts, heated to 50/C for 5 minutes and allowed to cool to room temperature over 30 minutes. The cassette was ligated as described above before ligating with pUC 18 plasmid which had been digested with restriction enzymes KpnI and XmaI. FIG. 2 shows the polynucleotide sequence of this DNA fragment.

Construction of Element 2: Tetracycline Resistance.

The structural gene of *S. aureus* tetM (Genbank accession number M21136) was amplified by PCR as described above, using primers CLQ463 and CLQ464 listed in Table I. These primers add unique recognition sites for the restriction enzymes BamHI and XmaI, respectively. The template for amplification was provided by Serban Iordanescu (Public Health Research Institute, NY), plasmid pRN6880, and is derived from the plasmids published by Nesin, M., Svec, P., Lupski, J. R., Godson, G. N., Kreiswirth, B., Kornblum, J. and Projan, S. J., *Antimicrob. Agents Chemother.*, 1990, 34:2273–2276. FIG. 3 shows the polynucleotide sequence of this DNA fragment.

Construction of Element 3: Tetracycline Repressor.

*E. coli* tetR (Genbank accession number J1830) was amplified by PCR using primers CLQ465 and CLQ467 or CLQ466 and CLQ467 from an *E. coli* strain carrying Tn10 (Hillen, W. and Schollmeier, K, *Nuc. Acids Res.*, 1983, 11:525–539). Primers CLQ465 and CLQ467 incorporate unique recognition sites for the restriction endonucleases SpeI and BamHI, respectively and include the wildtype promoter sequence for this gene. When primer CLQ466 is paired with CLQ467, it amplifies a shorter region of tetR, starting near the XbaI restriction enzyme recognition site found near the start codon of the gene. This shorter construct allows for the cloning of non-wildtype leader and promoter sequences to control this gene. PCR reactions were carried out using whole cells after heating the reaction mixture to 95/C for 5 minutes and cycling 35 times through three successive steps of 95/C for 1 minute, 45/C for 1 minute and 72/C for 1 minute. The PCR product was cloned using the pT7-Blue-T vector kit (Novagen, Madison, Wis.) according to the manufacturer's instructions. FIGS. 4a and 4b show the polynucleotide sequences of these DNA fragments.

Construction of Element 4: Transcriptional Promoters.

The synthetic promoter region contains two diverging transcription initiation signals and is derived from the one described by Geissendorfer and Hillen (*Appl. Microbiol. Biotechnol.*, 1990, 33:657–663). It was constructed from oligonucleotides shown in Table I as CLQ468, CLQ469, CLQ 470, CLQ471, CLQ472 and CLQ480. Conditions for kinasing, annealing and ligating these primers were as described for construction of Element 1. Oligonucleotides CLQ469, CLQ470, CLQ471, and CLQ472 were kinased before annealing CLQ469 with CLQ468, CLQ470 with CLQ471 and CLQ472 with CLQ480. After this annealing equimolar amounts of each pair was annealed with the other two pairs before ligation to each other and with pUC18 digested with restriction enzymes XbaI and PstI. When all 6 oligonucleotides were used to construct the promoter cassette, the tetR gene amplified with primers CLQ466 and CLQ467 was ligated to it and tetR will be transcribed from non-wild-type leader and promoter sequences. Alternatively, when the wildtype promoter and leader sequence from the tetR gene was included on the PCR fragment (using PCR primers CLQ465 and CLQ467 for amplification), the synthetic promoter element constructed with only oligonucleotides CLQ470, CLQ471, CLQ472 and CLQ473 was ligated to it. FIG. 5 shows the polynucleotide sequence of this DNA fragment.

Construction of Element 5: Reporter Gene.

The *S. aureas* BlaZ gene (Genbank accession number M15526), encoding beta-lactamase, was PCR amplified from plasmid pSA3800 (Novick, R. et al., *Cell,* 1989, 59, 395–404) using oligonucleotides CLQ486 and CLQ475 (element 5a) or CLQ486 and CLQ500 (element 5b) from Table 1. CLQ486 incorporates a unique recognition sequence for the restriction endonuclease PstI. CLQ475 includes unique recognition sites for the restriction endonucleases SphI and EcoRI. CLQ500 includes unique recognition sites for the restriction endonuclease PmeI. The PCR products were cloned using the pT7-Blue-T vector kit (Novagen, Madison, Wis.). FIGS. 6a and 6b show the polynucleotide sequence of these DNA fragments.

After all the PCR and synthetic DNA elements are assembled into a single cassette, the DNA cassette is ligated in a *S. aureus* plasmid. For those constructs designed to integrate into the chromosome, the cassette is also ligated to insertion-directing sequences made of homologous chromosomal DNA. The plasmid is passaged through *S. aureus* RN4220, see Peng H., Novick, R. P., Kreiswirth, B., Kornblum, J. and Schievert, P., 1988, *J. Bacteriol.*, 170, 4365–4372, incorporated into this document by reference, a restriction minus, modification positive strain. Plasmid DNA purified from RN4220 is modified by native *S. aureus* DNA modification enzymes and is more readily transformed into pathogenic *S. aureus* strains that have wild-type DNA restriction systems, see Iordanescu, S. and Surdeanu, M., 1976, *J. Gen. Microbiol.*, 96, 277–281, incorporated into this document by reference. Insert DNA released by EcoRI restriction enzyme digestions is purified and circularized. This DNA is transformed into a pathogenic *S. aureus* strain, selecting for tetracycline resistance. Because the insert DNA does not have an origin of replication, it should not be maintained as an autonomous plasmid, and growth on tetracycline selects for recombinants where the cassette has been inserted into the chromosome. Southern Blots or PCR analysis are used to verify that the desired recombination event has occurred.

For regulation of a target gene on an autonomously replicating plasmid, the DNA cassette ligated into a suitable plasmid vector is passaged through *S. aureus* RN4220 for modification and then directly transformed intact into another *S. aureus* strain. This strain may be derived from a pathogenic strain but genetically engineered so that expression of the endogenous copy of the target gene is altered from the pathogenic parent.

Alternatively, the genes encoding tetracycline resistance and the tetracycline repressor with a promoter sequence can be recombined separately into another region of the *S. aureus* chromosome. These genes do not need to be adjacent to the other DNA elements of the regulatory cassette. The DNA elements containing the transcription terminators, tetracycline regulated promoter and the β-lactamase reporter gene can still be constructed so that they recombine between the target gene and its transcription regulatory elements on the wild-type chromosome.

The beta-lactamase reporter gene allows for measurement of transcriptional read-through at different tetracycline concentrations. If the tetracycline regulation works as expected in this system, the cells should make less beta-lactamase and the test gene at lower tetracycline concentrations. Ideally, no detectable levels of β-lactamase or the test gene would be found in the absence of tetracycline. If transcription of the test gene can be turned off in this way and the gene being tested is an essential gene, the cells should not survive in the absence of tetracycline. If the gene is not essential and appears to be regulated by tetracycline in this system, its potential as an antimicrobial target will be tested in an animal infection model. Animal infections are established with this genetically engineered bacteria while feeding tetracycline to the animals. We will look for clearing of the infection when tetracycline is removed from the infected animals' diet.

Example 1

In the first example, the validity of this approach is tested by controlling the regulation of a gene essential for *S. aureus* growth on minimal media lacking exogenous tryptophan: trpD, a gene encoding an enzyme of the tryptophan biosynthetic pathway. The structural gene for trpD from *S. aureus* chromosomal DNA was PCR amplified with specific primers adding polynucleotide sequences for recognition by PstI endonuclease to each end. This PCR construct is ligated between the promoter (element 4a or 4b) and the BlaZ structural gene (element 5b) so that it will be transcribed from left to right as drawn in FIG. 1. When cells are transformed with this construct, the trpD gene should be transcribed from the $P_{xyl}$ promoter and transformants can be selected for by growth on tetracycline. This example serves as a positive control for the regulatory system. If the regulatory elements function as predicted, the presence of tetracycline will allow transcription of the beta-lactamase marker gene as well as trpD, and the cells will grow on media with or with out ampicillin and with or without tryptophan. In the absence of tetracycline, the tet repressor should bind the promoter, decreasing transcription of beta-lactamase and trpD. In this case, the cells would not be expected to survive in the absence of ampicillin or tryptophan. If they do survive, levels of beta-lactamase produced by these cells can be measured at different tetracycline concentrations to determine the level of repression achieved with the tet repressor. As long as there is some repression, this control can be tested in the animal infection to see if an infection established by these cells in the presence of tetracycline can persist in the absence of tetracycline. This is an indicator for how sensitive the system will be in testing target genes.

Example 2

In the second example, the validity of integrating the cassette into the chromosome is tested by controlling the regulation of a gene assumed to be essential for S. aureus growth: the gene encoding elongation factor Tu (EF-Tu). EF-Tu is required for protein translation and is a proven target for antibiotics. (Selva, E., Montanini, N., Stella, S., Soffientini, A., Gastaldo, L. and Denaro, M., 1997, J. Antibiot. Tokyo 50, 22–26, incorporated by reference.) Primers CLQ455 and CLQ456 from Table 1 were used to PCR amplify one 320 base pair fragment from S. aureus chromosomal DNA corresponding to a region of DNA just upstream from the EF-Tu structural gene and including the 3' end of the structural gene for elongation factor G (FIG. 7a). A second fragment, PCR amplified using primers CLQ505 and CLQ506 from Table 1, corresponds to a region overlapping the 5' end of the EF-Tu structural gene (FIG. 7b). The insertional DNA cassette was constructed by ligating these fragments to element 1 and element 5a, respectively. When this DNA fragment is used to transform S. aureus cells, the fragments direct recombination of the insert into the chromosome about 20 bp before the putative ribosome binding site for the EF-Tu gene in the S. aureu chromosome. Insertion of the DNA fragment in the chromosome is selected by growth on tetracycline and ampicillin. Recombination into the desired site can be confirmed by Southern Blot or PCR analysis of chromosomal DNA. This example serves as a positive control for the regulatory system. If the regulatory elements function as predicted, the presence of tetracycline will allow transcription of the beta-lactamase marker gene as well as EF-Tu, and the cells will grow on media with or without ampicillin. In the absence of tetracycline, the tet repressor should bind the promoter, preventing transcription of beta-lactamase and EF-Tu. In this case, the cells would not be expected to survive in the presence or absence of ampicillin because EF-Tu is expected to be essential. If they do survive, levels of beta-lactamase produced by these cells can be measured at different tetracycline concentrations to determine the level of repression achieved with the tet repressor. As long as there is some repression, this control can be tested in the animal infection to see if an infection established by these cells in the presence of tetracycline can persist in the absence of tetracycline. This is an indicator for how sensitive the system will be in testing target genes.

Example 3

In the third example, the DNA cassette is constructed to allow testing of the S. aureus femA gene (Genbank accession number M23918). Elements 1, 2, 3, 4 and 5 are the same as the elements in Example 2. These elements were fused to two pieces of DNA corresponding to S. aureus chromosomal DNA around the femA structural gene. This gene has been identified as a virulence factor: insertional inactivations of the gene reduce the virulence of a S. aureus pathogen (Mei, J., Nourbakhsh, F, Ford, C. W., Holden, D. W., Mol. Microbiol., October 1997, 26(2):399–407). Primers CLQ451 and CLQ452 from Table 1 were used to amplify one 369 base pair fragment of S. aureus chromosomal DNA just upstream from the femA structural gene and including the 3' end of trpA (FIG. 8a). Primers CLQ501 and CLQ502 were used to amplify a second fragment of S. aureus chromosomal DNA overlapping the 5' end of the femA structural gene (FIG. 8b). Ligation of the first fragment to element 1 in the insertional DNA cassette and the second fragment to element 5a directs recombination of the insert into the chromosome about 25 bp before the putative ribosome binding site of femA in the S. aureus chromosome when cells are transformed with this construct. Again, insertion of the DNA fragment in the chromosome is selected by growth on tetracycline and ampicillin. Recombination into the desired site is confirmed by Southern Blot or PCR analysis of genomic DNA isolated from the recombinant cells. Variation in repression of beta-lactamase expression in the presence or absence of tetracycline is expected to be similar for that seen in Example 2. However, femA is reportedly not an essential gene for growth of the cells in vitro (Strandén, A. M., Ehlert, K., Labischinski, H., and Berger-Bachi, B., 1997, J. Bacteriol., 179:9–16), so these recombinant cells would be expected to grow even if transcription of BlaZ end femA is completely repressed in the absence of tetracycline. If femA is essential for the establishment of an infection and the absence of tetracycline prevents transcription of femA, these cells should not be able to establish an infection unless the animal has tetracycline in it. If femA is a good target for antibacterial agents, an infection with these cells established in the presence of tetracycline would be cleared with the subsequent removal of tetracycline.

Example 4

In the fourth example, the DNA cassette is constructed for insertion into the chromosome to allow testing of the lgt gene in S. aureus (Genbank accession number U35773). Encoding the first enzyme for the post-translational modification in lipoprotein biosynthesis, lgt has been shown to be an essential gene in E. coli (Gan, K, Sankaran, K, Williams, M. G., Aldea, M., Rudd, K E., Kushner, S. R., and Wu, H. C., 1995, J. Bacteriol. 177:1879–1882) and Salmonella typhimurium (Gan, K, Gupta, S. D., Sankaran, K, Schmid, M. B. and Wu, H. C., 1993, J. Biol. Chem. 268:16544–16550), incorporated by reference. However, the essential nature is believed due to toxic effects of unmodified pro-lipoprotein accumulation in the absence of lgt in these bacteria, and it is not yet known if lgt is an essential gene in S. aureus or if it is a gene required for infection. Primers CLQ453 and CLQ454 from Table 1 were used to PCR amplify a 450 base pair fragment from S. aureus chromosomal DNA corresponding to a region of DNA ending 15 bp upstream from the putative ribosomal binding site for the lgt structural gene (FIG. 9a). Primers CLQ503 and CLQ504 from Table 1 were used to PCR amplify another fragment of the S. aureus chromosome overlapping the 5' end of lgt (FIG. 9b). Ligation of this first fragment to element 1 and the second fragment to element 5a in the insertional DNA cassette directs recombination of the insert into the chromosome about 25 bp before the putative ribosome binding site of lgt in the S. aureus chromosome when cells are transformed with this construct. Again, insertion of the DNA fragment in the chromosome is selected by growth on tetracycline and ampicillin. Recombination into the desired site is confirmed by Southern Blot or PCR analysis of chromosomal DNA. Variation in repression of β-lactamase expression in the presence or absence of tetracycline is expected to be similar for that seen in Example 2. If transcription of BlaZ is repressed in the absence of tetracycline in this construct, lgt should also be repressed and the cells should grow only if lgt is not an essential gene. If it is not an essential gene, it can be tested in the animal infection model to determine if shutting off lgt transcription clears the infection.

TABLE 1

Synthetic oligonucleotides used in PCR amplification or cassette construction.

| NAME | SEQUENCE | |
|---|---|---|
| CLQ451 | ACGCACGAGCTCGGTTGCAGATGGCATTGTC | (SEQ ID NO:1) |
| CLQ452 | GGGGTACCCCCTCTGCAAATGTCAAA | (SEQ ID NO:2) |
| CLQ453 | ACGCACGAGCTCAGATCTTCGCTTGTGCGG | (SEQ ID NO:3) |
| CLQ454 | GGGGTACCCGCTGAAGAGATAGCGATTG | (SEQ ID NO:4) |
| CLQ455 | ACGCACGAGCTCTTTCAGAAATGTTCGGTTATG | (SEQ ID NO:5) |
| CLQ456 | GGGGTACCAAATTTATCTCTCATGATAG | (SEQ ID NO:6) |
| CLQ457 | CAGGTACAGCAGTAAGTAAGC | (SEQ ID NO:7) |
| CLQ458 | GTCAACGTGAGCGTAGTGACG | (SEQ ID NO:8) |
| CLQ459 | CGAAGTTTGATAGATGATACATTCTATTAAACTTCCTTTTTTTATGCTCTGAAA | (SEQ ID NO:9) |
| CLQ460 | AAACAATGATTATCTACCTTATTAGTGCAGATAGATAACCATTGTTTATC | (SEQ ID NO:10) |
| CLQ461 | AGCATAAAAAAAGGAAGTTTAATAGAATGTATCATCTATCAAACTTCGGTAC | (SEQ ID NO:11) |
| CLQ462 | CCGGGATAAACAATGGTTATCTATCTGCACTAATAAGGTAGATAATCATTGTTTTTTCAG | (SEQ ID NO:12) |
| CLQ463 | CGGGATCCAATGGAGGAAAATCACATG | (SEQ ID NO:13) |
| CLQ464 | TCCCCCCGGGTAGGACACAATATCCACTTGTAG | (SEQ ID NO:14) |
| CLQ465 | GACTAGTTTGACAAATAACTCTATCAATGATAGAGTGTC | (SEQ ID NO:15) |
| CLQ466 | TAATGATGTCTAGATTAGATAAAAGT | (SEQ ID NO:16) |
| CLQ467 | CGGGATCCTTAAGACCCACTTTCACATTT | (SEQ ID NO:17) |
| CLQ468 | CTAGACATCATTAATTCCTCCTTTTTGTTGACACTCTATCATTGATAGAGTTATTTGTCAAA | (SEQ ID NO:18) |
| CLQ469 | CTAGTTTGACAAATAACTCTATCAATGATAGTGTCAACAAAAAGGAGGAATTAATGATGT | (SEQ ID NO:19) |
| CLQ470 | CTAGTTTTTTATTTGTCGAGTTCATGAAAAACTAAAAAAAATTGAC | (SEQ ID NO:20) |
| CLQ471 | TTTTTTTTAGTTTTTCATGAACTCGACAAATAAAAAA | (SEQ ID NO:21) |
| CLQ472 | ACTCTATCATTGATAGAGTATAATTAAAATAAAAAAGCTGCA | (SEQ ID NO:22) |
| CLQ475 | ACATACGCATGCGAATTCTTAAAATTCCTTCATTACACTC | (SEQ ID NO:23) |
| CLQ480 | GCTTTTTTATTTTAATTATACTCTATCAATGATAGAGTGTCAA | (SEQ ID NO:24) |
| CLQ486 | AACTGCAGTAATATCGGAGGGTTTATTTTG | (SEQ ID NO:25) |
| CLQ500 | GTTTAAACTTAAAATTCTTCATTACACTC | (SEQ ID NO:26) |
| CLQ501 | GGAATTTTAAGTTTAAACTGCAAATACGGAAATGAAATTAAT | (SEQ ID NO:27) |
| CLQ502 | ACATACGCATGCGAATTCAAGTATTGATATGGTAAATATGG | (SEQ ID NO:28) |
| CLQ503 | GGAATTTTAAGTTTAAACGAGGAGTAGGTTGAATGGGTA | (SEQ ID NO:29) |
| CLQ504 | ACATACGCATGCGAATTCCTTGCGCTAAAATTATAC | (SEQ ID NO:30) |
| CLQ505 | GGAATTTTAAGTTTAAACGAATAGGAGAGATTTTATAATGGC | (SEQ ID NO:31) |
| CLQ506 | ACATACGCATGCGAATTCACGAGTTTGTGGCATTGGACC | (SEQ ID NO:32) |

What is claimed is:

1. A process for the identification of a microbial gene encoding a gene product that is important to a microbe's ability to infect or sustain an infection in a mammal, which process comprises:
   infecting a plurality of mammals with a microbe that bas been genetically altered such that the amount of said gene product produced by said genetically altered microbe is regulated by a Tetracycline-Controllable Element (TCE);
   where said TCE is a gene regulatory system that controls the expression of the target gene product through its ability to modulate the function of said gene in response to said microbe's exposure to tetracycline, and where said TCE is comprised of a tetracycline-controllable transcription promoter polynucleotide sequence;
   where said genetically altered microbe also comprises a polynucleotide sequence encoding a tetracycline resistance protein;
   where said polynucleotide sequence encoding a tetracycline resistance protein is contained on a tetracycline resistance and repressor DNA cassette (TRRDC), said TRRDC comprising a tetracycline repressor gene and a tetracycline resistance gene;
   where said TCE is operably linked to both a first polynucleotide sequence encoding a reporter gene (RG) and a second polynucleotide sequence comprising a target gene (TG);
   exposing the plurality of mammals to tetracycline;
   once an infection with the genetically altered microbe is establish, removing the tetracycline exposure of a portion of the plurality of mammals, such that a first group of the plurality of mammals is exposed to tetracycline and a second group of the plurality of mammals is not exposed to tetracycline; and
   comparing the degree of infection, microbe levels, or survival rates of the mammals in the first group and the second group wherein a difference between the two groups of animals in the survival rates levels of microbes, or levels of infection present identifies the gene product as important to a microbe's ability to infect or sustain an infection in a mammal.

2. The process of claim 1, where said tetracycline-controllable transcription promoter polynucleotide sequence is a prokaryotic transcription promoter.

3. The process of claim 1, where said reporter gene encodes a β-lactamase.

4. The process of claim 1, where the TCE, the TRRDC, the RG, and the TG are all on the same DNA cassette, referred to as a Regulatory DNA Cassette (RDC).

5. The process of claim 1, where said TRRDC promoter is operably linked to the TCE, the tetracycline repressor gene comprises the structural gene tetM, and the tetracycline resistance gene comprises the structural gene tetR.

6. The process of claim 1, where said difference between the two groups of animals is a difference in the levels of microbes or levels of infection present in the mammals.

7. The process of claim 1, where said difference between the two groups of animals is a difference in the survival rates of the groups of animals.

8. The process of claim 1, where said difference between the two groups of animals shows that animals exposed to tetracycline have poorer health, higher rates of infection, lower survival or higher levels of microbes than animals not exposed to tetracyline.

9. The process of claim 1, where said tetracycline resistance gene of said TRRDC comprises sequences from the *Staphylococcus aureus* tetM gene.

10. The process of claim 1, where said tetracycline repressor gene of said TRRDC is obtained from the Tn10 transposon.

11. The process of claim 1, where said TRRDC comprises the sequence of SEQ ID NO:35 or SEQ ID NO:36.

12. The process of claim 1, where said infected mammals are mice.

13. The process of claim 1, where said genetically altered microbe is a *Staphylococcus* species.

14. The process of claim 13, where said *Staphylococcus* species is *Staphylococcus aureus*.

15. The process of claim 1, where said microbe is a virus.

16. The process of claim 1, where said microbe is a lower eukaryote.

17. The process of claim 1, where said microbe is a yeast.

18. A process to regulate expression of a gene product by a microbe in a mammalian host with tetracycline or a tetracycline analog, said process comprising:
   infecting a mammalian host with a microbe that has been genetically altered such that the amount of said gene product produced by said genetically altered microbe is regulated by a Tetracycline-Controllable Element (TCE);
   where said TCE is a gene regulatory system that controls the expression of the target gene product through its ability to modulate the function of said gene in response to said microbe's exposure to tetracycline, and where said TCE is comprised of a tetracycline-controllable transcription promoter polynucleotide sequence;
   where said genetically altered microbe also comprises a polynucleotide sequence encoding a tetracycline resistance protein;
   where said polynucleotide sequence encoding a tetracycline resistance protein is contained on a tetracycline resistance and repressor DNA cassette (TRRDC), said TRRDC comprising a tetracycline repressor gene and a tetracycline resistance gene;
   where said TCE is operably linked to both a first polynucleotide sequence encoding a reporter gene (RG) and a second polynucleotide sequence comprising a target gene (TG); and
   exposing the mammalian host to tetracycline.

19. The process of claim 18, further comprising, once an infection with the genetically altered microbe is established, removing the tetracycline exposure of the mammalian host.

20. The process of claim 1, where said plurality of mammals are exposed to tetracycline while being infected with the genetically altered microbe.

21. The process of claim 1, where said plurality of mammals are exposed to tetracycline by adding tetracycline to the drinking water.

22. The process of claim 18, where the TCE, the TRRDC, the RG, and the TG are all on the same DNA cassette, referred to as a Regulatory DNA Cassette (RDC).

* * * * *